(12) United States Patent
Gregoris

(10) Patent No.: US 11,013,681 B2
(45) Date of Patent: May 25, 2021

(54) COSMETIC COMPOSITION

(71) Applicant: BAKEL SRL, Udine (IT)

(72) Inventor: Raffaella Gregoris, Udine (IT)

(73) Assignee: BAKEL SRL, Udine (IT)

( * ) Notice: Subject to any disclaimer, the term of this patent is extended or adjusted under 35 U.S.C. 154(b) by 0 days.

(21) Appl. No.: 15/744,885

(22) PCT Filed: Jul. 14, 2016

(86) PCT No.: PCT/IB2016/054201
§ 371 (c)(1),
(2) Date: Jan. 15, 2018

(87) PCT Pub. No.: WO2017/055943
PCT Pub. Date: Apr. 6, 2017

(65) Prior Publication Data
US 2018/0207085 A1 Jul. 26, 2018

(30) Foreign Application Priority Data

Jul. 15, 2015 (IT) ........................ 102015000034711

(51) Int. Cl.
*A61K 8/92* (2006.01)
*A61Q 19/00* (2006.01)
*A61K 8/04* (2006.01)
*A61K 8/06* (2006.01)

(52) U.S. Cl.
CPC .............. *A61K 8/922* (2013.01); *A61K 8/042* (2013.01); *A61K 8/06* (2013.01); *A61Q 19/00* (2013.01)

(58) Field of Classification Search
None
See application file for complete search history.

(56) References Cited

U.S. PATENT DOCUMENTS

| | | | | | |
|---|---|---|---|---|---|
| 3,906,108 | A | * | 9/1975 | Felty | A61K 8/671 514/560 |
| 3,996,388 | A | * | 12/1976 | Bellamy | A21D 10/04 426/552 |
| 4,034,122 | A | * | 7/1977 | Patterson | A23P 30/40 426/570 |
| 4,092,298 | A | * | 5/1978 | Humbert | C09D 133/14 524/904 |
| 4,216,242 | A | * | 8/1980 | Braverman | A23G 9/32 426/573 |
| 4,293,542 | A | * | 10/1981 | Lang | A61Q 17/04 424/47 |
| 4,315,912 | A | * | 2/1982 | Kalopissis | A61K 8/416 424/70.27 |
| 4,454,987 | A | * | 6/1984 | Mitchell | A61L 9/12 239/44 |
| 4,457,944 | A | * | 7/1984 | Conrad | A61K 8/31 424/59 |
| 4,769,234 | A | * | 9/1988 | Pines | A61K 8/64 424/172.1 |
| 4,789,744 | A | * | 12/1988 | Russell | C07C 51/487 504/258 |
| 4,846,463 | A | * | 7/1989 | Kleinnibbelink | A63B 69/18 482/71 |
| 4,948,577 | A | * | 8/1990 | Hara | A61K 8/498 424/59 |
| 4,994,266 | A | * | 2/1991 | Wells | A61L 9/05 239/53 |
| 5,000,937 | A | * | 3/1991 | Grollier | A61K 8/29 424/47 |
| 5,476,648 | A | * | 12/1995 | Fogel | A61Q 17/04 424/59 |
| 5,711,942 | A | * | 1/1998 | Eicken | A61K 8/361 424/195.11 |
| 5,800,818 | A | * | 9/1998 | Prugnaud | A61K 8/06 424/744 |
| 5,853,709 | A | * | 12/1998 | Willis | A61Q 9/02 424/73 |
| 6,013,255 | A | * | 1/2000 | Edens | A61K 8/06 424/439 |
| 6,211,393 | B1 | * | 4/2001 | Seguin | A61K 8/4913 556/410 |
| 7,238,377 | B2 | * | 7/2007 | Piccirilli | A61K 8/922 424/401 |
| 7,262,217 | B2 | * | 8/2007 | Baranger | A61K 8/368 514/400 |
| 2003/0165449 | A1 | * | 9/2003 | Kaczvinsky, Jr. | A61K 8/42 424/70.1 |

(Continued)

FOREIGN PATENT DOCUMENTS

FR 3015278 12/2013
KR 20090073622 * 7/2009 .............. A61K 8/19

(Continued)

OTHER PUBLICATIONS

"Macerating oils with Herbs", Soap Teacher, Nov. 2, 2010 (Nov. 2, 2010), XP002755440, Retrieved from the Internet: URL:http://soapteacher.blogspot.de/2010/11/macerating-oils-with-herbs.html [retrieved on Mar. 14, 2016] the whole document.
Database GNPD [Online] Mintel: Jun. 2015 (Jun. 2015), Superdrug: "Nutrient Plus Firming Serum", XP002766389, Database accesion No. 3232135 the whole document.
Database GNPD [Online] Mintel; Jun. 2015 (Jun. 2015). Superdrug: "Multiprotecting Serum", XP002766390, Database accession No. 3232135 the whole document.
Database GNPD [Online] Mintel; Aug. 2009 (Aug. 2009), Kracie Home: "Facial Emulsion", XP002766391, Database accession No. 1183291 the whole document.

(Continued)

*Primary Examiner* — Aradhana Sasan
(74) *Attorney, Agent, or Firm* — Rankin, Hill & Clark LLP

(57) ABSTRACT

Cosmetic composition for healing and treating the skin, the formula of which consists exclusively of compounds functional for the skin and/or compounds functional both for the skin and also for the structure of the formula.

4 Claims, No Drawings

(56) References Cited

U.S. PATENT DOCUMENTS

| | | | | |
|---|---|---|---|---|
| 2003/0211183 | A1* | 11/2003 | Takahashi | A61K 8/9789 424/770 |
| 2009/0238781 | A1* | 9/2009 | Sakuta | A61K 8/066 424/59 |
| 2009/0318570 | A1* | 12/2009 | Veeger | A61K 8/06 514/786 |
| 2010/0120911 | A1* | 5/2010 | Majeed | A61K 8/375 514/552 |
| 2011/0021439 | A1* | 1/2011 | Amari | A61K 8/922 514/18.8 |
| 2012/0128786 | A1* | 5/2012 | Saffie-Siebert | A61K 8/0279 424/600 |
| 2014/0335167 | A1* | 11/2014 | Panandiker | C07F 7/1804 424/451 |
| 2015/0050331 | A1* | 2/2015 | Needleman | A61K 38/1858 424/450 |
| 2015/0147357 | A1* | 5/2015 | Gan | A61K 31/734 424/278.1 |
| 2016/0317576 | A1* | 11/2016 | Rosanoff | A61K 47/36 |

FOREIGN PATENT DOCUMENTS

| | | | | |
|---|---|---|---|---|
| WO | WO-2014081939 | A1 * | 5/2014 | A61K 8/342 |
| WO | 2014168424 | | 10/2014 | |

OTHER PUBLICATIONS

Database GNPD [Online] Mintel; Jun. 2011 (Jun. 2011), Lida Refined: "Pores Refining Emulsion", XP002766392, Database accession No. 1582557 the whole document.

Database GNPD [Online] Mintel; May 10, 2013 (May 10, 2013), Coty Prestige: "Centifolia Rose Emulsion", XP002766393, Database accession No. 2066877 the whole document.

\* cited by examiner

COSMETIC COMPOSITION

FIELD OF THE INVENTION

Embodiments described here concern a cosmetic composition for looking after or treating the skin.

Hereafter, by cosmetic composition we mean a cream or ointment or generally spreadable cosmetic pastes, obtained in the form of an emulsion, a serum or fluid, an oleolite, water or gel.

BACKGROUND OF THE INVENTION

It is known that in the preparation of cosmetic compositions, for example spreadable ones, such as cream or in general cosmetic pastes, it is provided to use compounds functional for the skin and compounds exclusively functional for the structure of the formula.

Compounds functional for the skin are partly or completely absorbed by the skin and bring benefits for the parts of the body treated. In general, this type of compound represents the so-called active principles.

Compounds exclusively functional for the structure of the formula contribute to obtaining the cosmetic composition, whether it is an emulsion, serum, fluid, oleolite, water or gel.

The effects of a compound exclusively functional for the structure of the formula can affect the preservation method or the consistency of the cosmetic composition before it is used and/or at the moment of use, therefore when it is spread on the skin to be treated.

For example, a compound exclusively functional for the structure of the formula can make the cosmetic composition soft, fluid or viscous, and it allows to obtain a gel, to prevent any separation between the oily compounds and the aqueous compounds in an emulsion. Furthermore, exclusively functional compounds allow to preserve the cosmetic composition, especially in the presence of water.

The problem exists that many compounds used, as they are functional for the structure of the formula, do not bring any benefit for the skin, and can even entail a further deterioration of the skin treated. In fact, some of the compounds exclusively functional for the structure of the formula are indifferent to the skin, or can cause for example further drying of the skin, closing of the pores, or allergies, dermatitis or suchlike.

Among the compounds exclusively functional for the structure of the formula, there are for example silicons, petroleum jellies (for example paraffin), alcohols, perfumes, stabilizers, preservatives, emulsifiers, the main function of which is to confer on the formula of the cosmetic composition a "silken" effect in contact with the skin, and/or to confer stability on the oily parts, or increase the viscosity of formulas in gels and/or increase the softening and moisturizing effect of emulsions.

For example, one problem found with such compounds is the lack of dermo-compatibility, preventing the skin from breathing, and also leading for example to a progressive drying of the skin, closing of the pores and/or greater sensitivity.

It is also known that the presence of alcohols and preservatives allows on the one hand to preserve the cosmetic composition, but on the other hand increases sensitivity of the skin to develop dermatitis, allergies or similar pathologies.

There is therefore a need to perfect a cosmetic composition that can overcome at least one of the disadvantages of the state of the art.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

According to some embodiments, a cosmetic composition is provided for taking care of or treating the skin, the formula for which consists exclusively of compounds functional for the skin and/or compounds functional both for the skin and also for the structure of the formula. Furthermore, the cosmetic composition does not include compounds exclusively functional for the structure of the formula.

The present invention thus allows to obtain a cosmetic composition that provides to use only compounds functional at least for the skin, that is, a cosmetic composition in which, in a completely surprising and unusual way, there are compounds functional for the structure which also perform a functional and beneficial role for the skin, thus bringing an exclusive benefit for the skin, because either they are only active principals or possibly functional for the skin and also functional for the structure of the formula.

Moreover, with the present invention it is possible to obtain a cosmetic composition that provides to use only compounds that can be completely absorbed by the skin.

These and other aspects, characteristics and advantages of the present disclosure will be better understood with reference to the following description and attached claims.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

DETAILED DESCRIPTION OF SOME EMBODIMENTS

We shall now refer in detail to the various embodiments of the present invention. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

All the measurements were carried out, unless otherwise indicated, at 25° C. and at atmospheric pressure. All the temperatures, unless otherwise indicated, are expressed in degrees Celsius.

All the percentages and ratios indicated refer to the weight of the total composition (w/w), unless otherwise indicated.

All the percentage intervals reported here are supplied with the provision that the sum with respect to the overall composition is 100%, unless otherwise indicated.

All the intervals reported here shall be understood to include the extremes, including those that report an interval "between" two values, unless otherwise indicated.

The present description also includes the intervals that derive from uniting or overlapping two or more intervals described, unless otherwise indicated.

The present description also includes the intervals that can derive from the combination of two or more values taken at different points, unless otherwise indicated.

Terms such as "about", "generally", "substantially" and suchlike shall be understood with their function of modifying a term or value that is not absolute, but is not reported in the state of the art. Such terms shall be defined by the specific circumstances and by the terms that they are intended to modify according to the common acceptance of such terms in the specific field. They shall take into account at least the degree of experimental error expected, the technical error and the instrumental error for a given technique adopted to measure a value. Unless otherwise indicated, in the present description, singular forms such as "a", "an" and "one" shall be understood to include plural forms, unless the context suggests otherwise.

Embodiments described here concern a cosmetic composition for taking care of or treating the skin with a formula that consists exclusively of compounds functional for the skin, also called active principals, and/or compounds functional both for the skin and also functional for the structure of the formula. Moreover, the cosmetic composition does not include compounds exclusively functional for the structure of the formula.

Therefore, according to one aspect of the present invention, the cosmetic composition consists of compounds 100% w/w active and 100% w/w absorbable by the skin.

In a particular embodiment, the cosmetic composition can be an oleolite, or macerated oil, which provides to mix two or more substances in the form of fluid lipids. Depending on the type of fluid lipids used oils or butters can be obtained.

In one embodiment, an oleolite cosmetic composition can include one or more compounds functional for the skin, such as an energizer, a nutrient or a renewal.

Advantageously, one or more energizing compounds can coincide with refreshing and/or hydrating and/or solvent compounds.

Possible energizing compounds can be chosen from a group that can include, for example, *Eucalyptus globulus* leaf oil, *Mentha piperita* oil or limonene.

In particular, the energizing compounds also have a fragrance function for the structure of the cosmetic composition. Furthermore, limonene has a solvent function for the structure of the formula.

Advantageously, one or more nutrient compounds can coincide with compounds that have an emollient function for the skin and/or a fragrance and anti-oxidant functions for the structure of the cosmetic formula. A compound with these characteristics can be, for example, *Glycine soja* oil.

Advantageously, one or more renewal compounds can coincide with compounds having an abrasive function for the skin. A compound with these characteristics can be sea salt.

A possible formula can consist of the following compounds: *Eucalyptus globulus* leaf oil, *Mentha piperita* oil, limonene, *Glycine soja* oil and sea salt.

In particular, in the specific formula *Eucalyptus globulus* leaf oil goes from 0.1% to 1% w/w, *Mentha piperita* oil goes from 0.1% to 1% w/w, limonene goes from 0.1% to 1% w/w, *Glycine soja* oil goes from 10% to 25% w/w, and sea salt goes from 75% to 100% w/w.

For example, the oil can be made in order to obtain a cosmetic composition able to mechanically reduce the thickness of the dermis. Moreover, the cosmetic composition is able to stimulate circulation, especially in the event of swelling.

In one embodiment, an oleolite cosmetic composition can include one or more compounds functional for the skin, such as a nutrient, an anti-oxidant, a renewal or a balm.

Advantageously, one or more nutrient compounds can coincide with anti-ageing and/or hydrating compounds.

Possible nutrient compounds can be chosen from a group that can comprise, for example, *Prunus armeniaca* kernel oil, or *Helianthus annuus* seed oil.

In particular, some nutrient compounds can also have a fragrance function for the structure of the cosmetic composition.

Advantageously, one or more anti-oxidant compounds can coincide with compounds having an anti-ageing and/or hydrating function for the skin. A compound with these characteristics can be, for example, tocopheryl acetate.

Advantageously, one or more anti-oxidant compounds can coincide with compounds having a regenerative and/or hydrating function for the skin. A compound with these characteristics can be, for example, retinyl palmitate.

Advantageously, one or more renewal compounds can coincide with compounds having a protective function for the skin, and/or an absorbent, anti-aggregant, load agent, opaque-making, or suspendant function for the structure of the formula. A compound with these characteristics can be silica, for example.

Advantageously, one or more soothing compounds can coincide with compounds having a hydrating function for the skin and/or a fragrance function for the structure of the formula. A compound with these characteristics can be, for example, *Anthemis nobilis* oil.

A possible formula can consist of the following compounds: *Prunus armeniaca* kernel oil, tocopheryl acetate, silica, retinyl palmitate, *Helianthus annuus* seed oil or *Anthemis nobilis* oil.

In particular, in the specific formula *Prunus armeniaca* kernel oil goes from 75% to 100% w/w, tocopheryl acetate goes from 5% to 10% w/w, silica goes from 1% to 5% w/w, retinyl palmitate goes from 1% to 5% w/w, *Helianthus annuus* seed oil goes from 1% to 5% w/w and *Anthemis nobilis* oil is less than 0.1% w/w.

For example, the oil can be made in order to obtain a cosmetic composition for cleaning the skin without removing the hydrolipidic layer that covers and protects the skin.

In one embodiment, an oleolite cosmetic composition can include one or more compounds functional for the skin, such as an anti-oxidant, a nutrient, an anti-ageing and an active de-makeup compound.

Advantageously, one or more anti-oxidant compounds can coincide with renewal and/or hydrating compounds. A compound with these characteristics can be retinyl palmitate for example.

Advantageously again, one or more anti-oxidant compounds can coincide with anti-ageing and/or hydrating compounds. A compound with these characteristics can be tocopheryl acetate, for example.

Advantageously, one or more nutrient compounds can coincide with compounds having an anti-oxidant and/or hydrating function for the skin.

Possible nutrient compounds can be chosen from a group that can comprise, for example, *Oryza sativa* bran oil and *Helianthus annuus* seed oil.

Advantageously, one or more anti-ageing compounds can coincide with compounds having a soothing function for the skin. A compound with these characteristics can be *Oryza sativa* bran extract for example.

Advantageously, one or more active de-makeup compounds can coincide with compounds having an emollient function for the skin. A compound with these characteristics can be coco-caprylate.

A possible formula can consist of the following compounds: *Oryza sativa* bran oil, coco-caprylate, *Helianthus annuus* seed oil, *Avena sativa* bran extract, retinyl palmitate and tocopheryl acetate.

In particular, in the specific formula *Oryza sativa* bran oil goes from 50% to 75% w/w, coco-caprylate goes from 25% to 50% w/w, *Helianthus annuus* seed oil goes from 1% to 5% w/w, *Avena sativa* bran extract is less than 0.1% w/w, retinyl palmitate goes from 0.1% to 1% w/w and tocopheryl acetate goes from 0.1% to 1% w/w.

For example, the oil can be made in order to obtain a cosmetic composition for cleaning the skin without removing the hydrolipidic layer that covers and protects the skin.

In one embodiment, an oleolite cosmetic composition can include one or more compounds functional for the skin, such as a nutrient, an emollient, an anti-oxidant, an elasticizer, a softener and a balm.

Advantageously, one or more nutrient compounds can coincide with hydrating compounds for the skin.

Possible nutrient compounds for the skin can be chosen from a group that can comprise, for example, *Oryza sativa* bran oil, caprylic and/or capric triglyceride, *Butyrospermum parkii* butter and *Prunus armeniaca* kernel oil.

In particular, the nutrient compounds can also have a fragrance function for the structure of the cosmetic composition. Compounds with these characteristics can be caprylic and/or capric triglyceride, and *Prunus armeniaca* kernel oil for example.

Advantageously, one or more emollient compounds can coincide with compounds having a hydrating function for the skin and/or a fragrance function for the structure of the cosmetic formula. Compounds with these characteristics can be glyceryl dibehenate and cetyl palmitate for example.

Advantageously, one or more anti-oxidant compounds can coincide with compounds having a hydrating function for the skin. Compounds with these characteristics can be tocopheryl acetate, tocopherol, and limonene for example. Moreover, limonene and tocopherol also have a fragrance function for the structure of the formula. Furthermore, limonene also has a solvent function for the structure of the formula.

Advantageously, one or more elasticizer compounds can coincide with compounds having a hydrating function for the skin. Compounds with these characteristics can be linolenic acid, linoleic acid and arachidonic acid, for example. Furthermore, linolenic acid and linoleic acid can also have a surfactant function and a fragrance function for the structure of the formula.

Advantageously, one or more softening compounds can be *Stevia rebaudiana* leaf and/or stem extract and aroma for example. Moreover, *Stevia rebaudiana* leaf and/or stem extract also has an aromatizing function for the structure of the formula.

Advantageously, one or more elasticizer compounds can coincide with compounds having an anti-oxidant function for the skin. One compound with these characteristics can be *Melaleuca alternifolia* leaf oil for example. Moreover, *Melaleuca alternifolia* leaf oil also has a fragrance function for the structure of the formula.

A possible formula can consist of the following compounds: *Oryza sativa* bran oil, caprylic and/or capric triglyceride, *Butyrospermum parkii* butter, glyceryl dibehenate, *Prunus armeniaca* kernel oil, tocopheryl acetate, cetyl palmitate, aroma, linolenic acid, linoleic acid, arachidonic acid, tocopherol, *Melaleuca alternifolia* leaf oil, *Stevia rebaudiana* leaf and/or stem extract or limonene.

In particular, in the specific formula, *Oryza sativa* bran oil goes from 25% to 50% w/w, caprylic and/or capric triglyceride goes from 10% to 25% w/w, *Butyrospermum parkii* butter goes from 10% to 25% w/w, glyceryl dibehenate goes from 10% to 25% w/w, *Prunus armeniaca* kernel oil goes from 5% to 10% w/w, tocopheryl acetate goes from 0.1% to 1% w/w, cetyl palmitate goes from 0.1% to 1% w/w, aroma goes from 0.1% to 1% w/w, linolenic acid goes from 0.1% to 1% w/w, linoleic acid goes from 0.1% to 1% w/w, arachidonic acid goes from 0.1% to 1% w/w, tocopherol goes from 0.1% to 1% w/w, *Melaleuca alternifolia* leaf oil is less than 0.1% w/w, *Stevia rebaudiana* leaf and/or stem extract is less than 0.1% w/w and limonene is less than 0.1% w/w.

For example, the butter can be made in order to obtain a cosmetic composition able to nourish, protect and improve the elasticity of the skin.

In one embodiment, an oleolite cosmetic composition can include one or more compounds functional for the skin, such as a nutrient, an emollient, an anti-ageing compound, an energizing complex, an elasticizer and an anti-oxidant.

Advantageously, one or more nutrient compounds can coincide with elasticizer compounds for the skin. Moreover, nutrient compounds for the skin can coincide with elasticizer and hydrating compounds for the skin.

Possible nutrient compounds for the skin can be chosen from a group which can include *Argania spinosa* kernel oil, *Gossypium herbaceum* seed oil, *Shorea robusta* seed butter, caprylic and/or capric triglyceride, linseed acid, squalene, linolenic acid, linoleic acid, phytosterols and arachidonic acid for example.

In particular, some nutrient compounds can also have a fragrance and/or surfactant function for the structure of the cosmetic composition. Compounds with these characteristics can be caprylic and/or capric triglyceride or linseed acid for example.

Advantageously, one or more emollient compounds can coincide with compounds having a hydrating function for the skin and/or viscous-making functions for the structure of the cosmetic formula. Compounds with these characteristics can be hydrogenated vegetable oil and hydrogenated castor oil, for example.

Advantageously, one or more anti-ageing compounds can coincide with compounds having an anti-oxidant and/or hydrating UV ray absorbent function for the skin and/or fragrance function for the structure of the cosmetic formula. Compounds with these characteristics can be tocopheryl acetate, tocotrienols, tocopherol, and ubiquinone for example.

Advantageously, one or more compounds with an energizing complex function can coincide with compounds having a hydrating function for the skin and/or a fragrance function for the structure of the formula. Compounds with these characteristics can be *Aurantium bergamia* peel oil, *Citrus aurantium dulcis* peel oil, *Citrus limon* peel oil, *Copaifera officinalis* resin and *Cymbopogon citratus* leaf oil for example.

In particular, some compounds with an energizing complex function for the skin can also have a filmogenic function for the structure of the formula. Furthermore, *Copaifera officinalis* resin also has a filmogenic function for the structure of the formula.

Advantageously, one or more elasticizer compounds can coincide with compounds having a hydrating function for the skin. For example, *Elaeis guineensis* oil.

Advantageously, one or more solely anti-oxidant compounds for the skin can coincide with compounds having a colorant function for the structure of the formula, for example beta carotene.

A possible formula can consist of the following compounds: *Argania spinosa* kernel oil, *Gossypium herbaceum* seed oil, *Shorea robusta* seed butter, hydrogenated vegetable oil, hydrogenated castor oil, caprylic and/or capric triglyceride, tocopheryl acetate, *Citrus aurantium bergamia* peel oil, *Citrus aurantium dulcis* peel oil, *Citrus limon* peel oil, *Copaifera officinalis* resin, *Cymbopogon citratus* leaf oil, tocotrienols, *Elaeis guineensis* oil, linseed acid, tocopherol, squalene, linolenic acid, linoleic acid, phytosterols, arachidonic acid, beta carotene and ubiquinone.

In particular, in the specific formula, *Argania spinosa* kernel oil goes from 25% to 50% w/w, *Gossypium herbaceum* seed oil goes from 10% to 25% w/w, *Shorea robusta* seed butter goes from 10% to 25% w/w, hydrogenated vegetable oil goes from 5% to 10% w/w, hydrogenated castor oil goes from 5% to 10% w/w, caprylic and/or capric triglyceride goes from 1% to 5% w/w, tocopheryl acetate goes from 0.1% to 1% w/w, *Citrus aurantium bergamia* peel oil is less than 0.1% w/w, *Citrus aurantium dulcis* peel oil goes from 0.1% to 1% w/w, *Citrus limon* peel oil goes from 0.1% to 1% w/w, *Copaifera officinalis* resin is less than 0.1% w/w, *Cymbopogon citratus* leaf oil is less than 0.1% w/w, tocotrienols goes from 0.1% to 1% w/w, *Elaeis guineensis* oil is less than 0.1% w/w, linseed acid is less than 0.1% w/w, tocopherol goes from 0.1% to 1% w/w, squalene goes from 0.1% to 1% w/w, linolenic acid goes from 0.1% to 1% w/w, linoleic acid goes from 0.1% to 1% w/w, phytosterols goes from 0.1% to 1% w/w, arachidonic acid goes from 0.1% to 1% w/w, beta carotene is less than 0.1% w/w and ubiquinone is less than 0.1% w/w.

For example, the butter can be made in order to obtain a cosmetic composition able to increase the elasticity and tone of the skin.

In a particular embodiment, the cosmetic composition can be a solution in which water-soluble salts, extracts and/or substances are dissolved in a solvent functional for the structure of the formula, for example water or water mixed with alcohols or hydrophilic compounds in general.

Hereafter we will refer to a cosmetic composition in the form of an aqueous solution, in which the solvent is water, or hydrophilic compounds also functional for the skin and not harmful for it.

In some embodiments, combinable with all the embodiments described here, the cosmetic composition can comprise a solvent with a moisturizing, hydrating and/or emollient function for the skin.

In one embodiment, a cosmetic composition in solution can include one or more compounds functional for the skin, such as a moisturizer, a refresher, a deodorant, a purifier, a pH adjuster, an anti-oxidant, an astringent or an emollient.

Advantageously, one or more moisturizing compounds can coincide with hydrating compounds for the skin. Moreover, nutrient compounds for the skin can coincide with solvent and/or surfactant compounds for the structure of the formula.

Possible moisturizing compounds for the skin can be chosen from a group that can include, for example, sterile and demineralized water and sulfated castor oil.

Advantageously, the water also has a hydrating function for the skin and/or a solvent function for the structure of the formula.

Advantageously, sulfated castor oil also has a surfactant function for the structure of the formula.

Advantageously, one or more refreshing compounds can coincide with purifying and/or hydrating compounds for the skin. Moreover, refreshing compounds for the skin can coincide with compounds with a fragrance function for the structure of the formula.

Possible refreshing compounds for the skin can be chosen from a group that can comprise *Mentha piperita* oil and *Eucalyptus globulus* leaf oil, for example.

Advantageously, one or more deodorant compounds can coincide with compounds having a fragrance function for the structure of the formula. Moreover, deodorant compounds for the skin can coincide with compounds with a solvent and/or plastifying function for the structure of the formula.

Possible deodorant compounds for the skin can be chosen from a group that can comprise triethyl citrate, ethyl lauroyl arginate HCl, limonene and linalool for example.

Advantageously, one or more purifying compounds can coincide with compounds having an anti-oxidant and/or biocide and/or fragrance function for the structure of the formula.

Possible purifying compounds for the skin can be chosen from a group that can comprise *Melaleuca alternifolia* leaf oil or Piroctone olamine for example.

Advantageously, one or more pH adjuster compounds can coincide with compounds having a protective and/or deodorant and/or emollient function for the skin. For example, bicarbonate of soda and lactic acid. Moreover, bicarbonate of soda also has a deodorant and protective function for the skin, and an abrasive and buffer agent function for the structure of the formula. Furthermore, lactic acid also has an exfoliant, moisturizing and hydrating function for the skin and a fragrance function for the structure of the formula.

Advantageously, one or more anti-oxidant compounds can coincide with compounds having a soothing and/or hydrating function for the skin. For example, *Malva sylvestris* extract.

Advantageously, one or more astringent compounds can coincide with compounds having an anti-perspiration function for the skin and/or a fragrance function for the structure of the formula. For example, *Salvia officinalis* oil.

Advantageously, one or more emollient compounds can coincide with moisturizing and/or protective compounds for the skin and/or fragrance and/or viscosity-reducing compounds for the structure of the formula. For example, glycerin.

A possible formula can consist of the following compounds: sterilized and demineralized water, sulfated castor oil, *Malva sylvestris* extract, triethyl citrate, sodium bicarbonate, ethyl lauroyl arginate HCl, lactic acid, *Melaleuca alternifolia* oil, *Mentha piperita* oil, *Eucalyptus globulus* leaf oil, *Salvia officinalis* oil, piroctone olamine, vegetable glycerin, limonene and linalool.

In particular, in the specific formula, sterilized and demineralized water goes from 75% to 100% w/w, sulfated castor oil goes from 10% to 25% w/w, *Malva sylvestris* extract goes from 1% to 5% w/w, triethyl citrate goes from 1% to 5% w/w, sodium bicarbonate goes from 1% to 5% w/w, ethyl lauroyl arginate HCl goes from 0.1% to 1% w/w, lactic acid is less than 0.1% w/w, *Melaleuca alternifolia* oil is less than 0.1% w/w, *Mentha piperita* oil goes from 0.1% to 1% w/w, *Eucalyptus globulus* leaf oil is less than 0.1% w/w, *Salvia*

*officinalis* oil is less than 0.1% w/w, piroctone olamine is less than 0.1% w/w, vegetable glycerin goes from 0.1% to 1% w/w, limonene is less than 0.1% w/w and linalool is less than 0.1% w/w.

For example, the solution can be made in order to obtain a cosmetic composition able to maintain the equilibrium of the skin and to prevent irritations.

In one embodiment, a cosmetic composition in solution can include one or more compounds functional for the skin, such as a moisturizer, a deodorant, an anti-ageing compound or an anti-oxidant.

Advantageously, one or more moisturizing compounds can coincide with hydrating compounds for the skin. Moreover, nutrient compounds for the skin can coincide with solvent compounds for the structure of the formula.

A possible moisturizer for the skin can be water, for example.

Advantageously, one or more deodorant compounds can coincide with hydrating compounds. Moreover, deodorant compounds for the skin can coincide with compounds with a fragrance and/or plastifying and/or solvent and/or anti-oxidant and/or filmogenic and/or aromatizing function for the structure of the formula.

Possible deodorant compounds for the skin can be chosen from a group which can comprise *Citrus aurantium dulcis* fruit extract, triethyl citrate, limonene, *Citrus aurantium dulcis* peel oil, *Citrus limon* peel oil, *Citrus aurantium bergamia* peel oil, sodium bicarbonate, *Melaleuca alternifolia* leaf oil, *Copaifera officinalis* resin, *Cymbopogon citratus* leaf oil, citral, linalool and geraniol for example. Moreover, sodium bicarbonate also has an abrasive, buffer agent, deodorant, pH adjuster and protection function for the skin.

An anti-ageing compound can be cocoyl proline for example.

An anti-oxidant compound can be hydroxyacetophenone for example.

A possible formula can consist of the following compounds: *Citrus aurantium dulcis* fruit extract, cocoyl proline, triethyl citrate, sterilized and demineralized water, hydroxyacetophenone, limonene, *Citrus aurantium dulcis* peel oil, *Citrus limon* peel oil, *Citrus aurantium bergamia* peel oil, sodium bicarbonate, *Melaleuca alternifolia* leaf oil, *Copaifera officinalis* resin, *Cymbopogon citratus* leaf oil, citral, linalool and geraniol.

In particular, in the specific formula, *Citrus aurantium dulcis* fruit extract goes from 75% to 100% w/w, cocoyl proline goes from 1% to 5% w/w, triethyl citrate goes from 1% to 5% w/w, sterilized and demineralized water goes from 1% to 5% w/w, hydroxyacetophenone goes from 0.1% to 1% w/w, limonene goes from 0.1% to 1% w/w, *Citrus aurantium dulcis* peel oil goes from 0.1% to 1% w/w, *Citrus limon* peel oil goes from 0.1% to 1% w/w, *Citrus aurantium bergamia* peel oil goes from 0.1% to 1% w/w, sodium bicarbonate is less than 0.1% w/w, *Melaleuca alternifolia* leaf oil is less than 0.1% w/w, *Copaifera officinalis* resin is less than 0.1% w/w, *Cymbopogon citratus* leaf oil is less than 0.1% w/w, citral is less than 0.1% w/w, linalool is less than 0.1% w/w and geraniol is less than 0.1% w/w.

For example, the solution can be made in order to obtain a cosmetic composition able to maintain the equilibrium of the skin and to prevent irritations.

In one embodiment, a cosmetic composition in solution can include one or more compounds functional for the skin, such as a hydrating compound, an anti-oxidant, an anti-ageing, a protective and an illuminator compound.

Possible hydrating compounds for the skin can be chosen from a group that can comprise vegetable glycerin, mannitol, sterilized and demineralized water. Moreover, vegetable glycerin can have a moisturizing and/or protective function for the skin and a fragrance, moisturizing and viscosity-reducing function for the structure of the formula. Moreover, mannitol has a binding, aromatizing and moisturizing function for the structure of the formula. Furthermore, water also has a solution function for the structure of the formula.

Advantageously, one or more hydrating compounds can also have a soothing and/or anti-oxidant function for the skin. Possible hydrating compounds with these additional functions for the skin can be chosen from a group that can include *Hamamelis virginiana* water, *Aloe barbadensis* leaf juice, *Lilium candidum* flower water, *Rosa canina* fruit extract and *Rubus idaeus* leaf extract. These hydrating compounds can also have an astringent and/or protective and/or emollient function.

A possible anti-oxidant for the skin can be for example hydroxyacetophenone.

Advantageously, one or more anti-ageing compounds can also have a fragrance and/or solvent function for the structure of the formula.

Possible anti-ageing compounds for the skin can be chosen from a group that includes cocoyl proline, *Jasminum officinale* oil, linalool, benzyl benzoate and acetyl tetrapeptide-11.

A possible protective for the skin, which advantageously also has a pH adjuster function, can be dipotassium phosphate for example.

A possible illuminator for the skin, which advantageously also has a pH adjuster function for the skin and fragrance function and/or chelation agent for the structure of the formula, can be citric acid for example.

In particular, vegetable glycerin, *Rosa canina* fruit extract, and *Rubus idaeus* leaf extract are vegetable products obtained from biological agriculture.

A possible formula can consist of the following compounds: *Hamamelis virginiana* water, *Aloe barbadensis* leaf juice, *Lilium candidum* flower water, vegetable glycerin, mannitol, sterilized and demineralized water, hydroxyacetophenone, cocoyl proline, *Rosa canina* fruit extract, dipotassium phosphate, citric acid, *Rubus idaeus* leaf extract, *Jasminum officinale* oil, linalool, benzyl benzoate and acetyl tetrapeptide-11.

In particular, in the specific formula, *Hamamelis virginiana* water goes from 75% to 100% w/w, *Aloe barbadensis* leaf juice goes from 5% to 10% w/w, *Lilium candidum* flower water goes from 1% to 5% w/w, vegetable glycerin goes from 1% to 5% w/w, mannitol goes from 1% to 5% w/w, sterilized and demineralized water goes from 1% to 5% w/w, hydroxyacetophenone goes from 0.1% to 1% w/w, cocoyl proline goes from 0.1% to 1% w/w, *Rosa canina* fruit extract is less than 0.1% w/w, dipotassium phosphate is less than 0.1% w/w, citric acid is less than 0.1% w/w, *Rubus idaeus* leaf extract is less than 0.1% w/w, *Jasminum officinale* oil is less than 0.1% w/w, linalool is less than 0.1% w/w, benzyl benzoate is less than 0.1% w/w and acetyl tetrapeptide-11 is less than 0.1% w/w.

For example, the solution can be made in order to obtain a cosmetic composition able to hydrate, soothe, revitalize and illuminate the skin. Moreover, the cosmetic composition is able to restore skin hydration, contrast dilated pores and perform an anti-oxidant action to render the skin compact and tonic.

In one embodiment, a cosmetic composition in solution can include one or more compounds functional for the skin, such as a hydrating compound, emollient, washing active, skin pH adjuster and balm.

Possible hydrating compounds for the skin can be chosen from a group that can include vegetable glycerin, rhamnose, glucose, glucuronic acid, xylitol, and mannose, sterilized and demineralized water.

Advantageously, one or more hydrating compounds can also have a moisturizing and/or protective and/or pH adjuster for the skin and fragrance and/or aromatizing and/or viscosity-reducing and/or chelation agent and/or solvent for the structure of the formula.

Advantageously, one or more emollient compounds can also have a solvent and/or viscosity-reducing function for the structure of the formula. Possible emollient compounds with these functions can be chosen from a group that can include ethyl lauroyl arginate HCl and propanediol.

A possible washing active for the skin which can advantageously also have an emollient function for the skin and/or a surfactant-emulsifying function for the structure of the formula, can be polyglyceryl-4 caprate for example.

Advantageously, one or more skin pH adjuster compounds can also have a denaturing function for the structure of the formula. A possible skin pH adjuster can be sodium hydroxide for example.

A possible balm for the skin, which advantageously also has a toning function, can be *Rosa centifolia* flower water for example.

A possible formula can consist of the following compounds: *Rosa centifolia* flower water, polyglyceryl-4 caprate, vegetable glycerin, ethyl lauroyl arginate HCl, propanediol, rhamnose, glucose, glucuronic acid, xylitol, mannose, sterilized and demineralized water and sodium hydroxide.

In particular, in the specific formula, *Rosa centifolia* flower water goes from 75% to 100% w/w, polyglyceryl-4 caprate goes from 1% to 5% w/w, vegetable glycerin goes from 0.1% to 1% w/w, ethyl lauroyl arginate HCl goes from 0.1% to 1% w/w, propanediol goes from 0.1% to 1% w/w, rhamnose is less than 0.1% w/w, glucose is less than 0.1% w/w, glucuronic acid is less than 0.1% w/w, xylitol goes from 0.1% to 1% w/w, mannose goes from 0.1% to 1% w/w, sterilized and demineralized water goes from 0.1% to 1% w/w and sodium hydroxide is less than 0.1% to 1% w/w.

For example, the solution can be made in order to obtain a cosmetic composition for cleaning the skin without removing the hydrolipidic layer that covers and protects the skin.

In one embodiment, a cosmetic composition in solution can be used to make moistened tissues for treating the skin.

The cosmetic composition in solution can include one or more compounds functional for the skin, such as a balm, an illuminator, a renewal, a skin pH adjuster, an anti-oxidant.

A possible balm for the skin, which advantageously can also have a hydrating function for the skin and a fragrance function for the structure of the formula, can be *Tilia cordata* flower water for example.

A possible illuminator for the skin, which advantageously can also have an anti-ageing and pH adjuster function for the skin and a fragrance and chelation agent function for the structure of the formula, can be citric acid for example.

Possible renewal compounds for the skin can be chosen from a group that can include malic acid and salicylic acid.

Advantageously, one or more renewal compounds can also have an anti-ageing and/or pH adjuster and/or anti-acne and/or exfoliant and/or hydrating function for the skin and a fragrance and/or denaturing function for the structure of the cosmetic composition.

Possible pH adjuster compounds for the skin can be chosen from a group that can include sodium hydroxide and sodium bicarbonate.

Moreover, sodium hydroxide can also have a denaturing function for the structure of the formula.

Furthermore, sodium bicarbonate can also have an abrasive, deodorant and protective function for the skin and a buffer agent function for the structure of the formula.

A possible anti-oxidant for the skin, which advantageously can also have a soothing and hydrating function for the skin, can be *Helichrysum italicum* flower water for example.

A possible formula can consist of the following compounds: *Tilia cordata* flower water, citric acid, malic acid, salicylic acid and sodium hydroxide.

In particular, in the specific formula, *Tilia cordata* flower water goes from 75% to 100% w/w, citric acid goes from 0.1% to 1% w/w, malic acid goes from 0.1% to 1% w/w, salicylic acid is less than 0.1% w/w, and sodium hydroxide goes from 0.1% to 1% w/w.

For example, the solution can be made in order to obtain a treatment of the skin that eliminates the dead cells and stimulates cell renewal. Moreover, the cosmetic composition gives luminosity to the skin and eliminates thickening of the skin.

Another possible formula can consist of the following compounds: *Helichrysum italicum* flower water and sodium bicarbonate.

In particular, in the specific formula *Helichrysum italicum* flower water goes from 75% to 100% w/w and sodium bicarbonate goes from 0.1% to 1% w/w.

For example, the solution can be made in order to obtain a treatment that restores the physiological pH, rebalancing the skin.

In a particular embodiment, the cosmetic composition can be a monophase gel consisting of an aqueous or hydro-alcohol solution made viscous by a jellifying additive with a viscous-making function for the structure of the formula.

Hereafter we will refer to a cosmetic composition in the form of an aqueous gel in which the solvent, if present, is water, or hydrophilic compounds also functional for the skin and in which the jellifying additive is functional not only for the structure of the formula but also for the skin.

In one embodiment, a cosmetic composition in gel form can include one or more compounds functional for the skin, such as an exfoliant, an emollient, a hydrating, anti-oxidant, illuminator or moisturizing compound.

Possible exfoliant compounds for the skin can be chosen from a group that can include citric acid, salicylic acid, phytic acid and mandelic acid. Moreover, the citric acid can also have an illuminator and/or pH adjuster function for the skin and the function of a chelation agent and fragrance function for the structure of the formula.

Advantageously, one or more exfoliant compounds can also have a renewal and/or anti-acne and/or exfoliant and/or hydrating function for the skin and a fragrance and/or denaturing and/or chelation agent function for the structure of the formula.

A possible emollient for the skin can be ethyl lauroyl arginate HCl for example.

A possible hydrating compound for the skin, which can advantageously also have a protective function for the skin and a moisturizing and/or fragrance and/or viscosity-reducing function for the structure of the formula can be vegetable glycerin for example.

A possible anti-oxidant for the skin, which can advantageously also have a hydrating function for the skin and fragrance function for the structure of the formula, can be *Tilia cordata* water for example.

A possible illuminator for the skin, which can advantageously also have a pH adjuster function for the skin and a fragrance and/or buffer agent and/or chelation agent function for the structure of the formula, can be sodium citrate for example.

A possible moisturizer for the skin, which can advantageously also have a binding and/or stabilizing and/or film-ogenic and/or aqueous viscous-making function for the structure of the formula can be hydroxyethylcellulose for example.

A possible formula can consist of the following compounds: *Tilia cordata* water, sodium citrate, citric acid, hydroxyethylcellulose, salicylic acid, phytic acid, mandelic acid, vegetable glycerin and ethyl lauroyl arginate HCl.

In particular, in the specific formula *Tilia cordata* water goes from 75% to 100% w/w, sodium citrate goes from 5% to 10% w/w, citric acid goes from 1% to 5% w/w, hydroxyethylcellulose goes from 1% to 5% w/w, salicylic acid goes from 0.1% to 1% w/w, phytic acid goes from 0.1% to 1% w/w, mandelic acid goes from 0.1% to 1% w/w, vegetable glycerin goes from 0.1% to 1% w/w and ethyl lauroyl arginate HCl goes from 0.1% to 1% w/w.

For example, the gel can be made in order to obtain a cosmetic composition able to promote cell regeneration to confer luminosity and uniformity on the skin.

In one embodiment, a cosmetic composition in gel form can include one or more compounds functional for the skin, such as a hydrating compound, a balm, a washing active, an anti-ageing, a renewal, an emollient.

Possible hydrating compounds for the skin can be chosen from a group that can include *Aloe barbadensis* leaf juice and vegetable glycerin. Moreover, the *Aloe barbadensis* leaf juice can also have an anti-oxidant function for the skin. Furthermore, the vegetable glycerin can have a protective function for the skin and a fragrance and/or moisturizing and/or viscosity-reducing function for the structure of the formula.

Advantageously, one or more soothing compounds can also have a hydrating and/or protective and/or astringent function for the skin.

Possible soothing compounds for the skin can be chosen from the group that can include *Centaurea cyanus* flower water and *Hamamelis virginiana* water.

A possible washing active for the skin can be coco-glucoside for example, which advantageously also has a surfactant function for the structure of the formula.

A possible anti-ageing compound for the skin, which advantageously can also have a hydrating function for the skin and a fragrance function for the structure of the formula, can be arginine for example.

A possible renewal compound for the skin, which advantageously can also have a pH adjuster function for the skin and a fragrance function for the structure of the formula, can be malic acid for example.

Possible emollient compounds for the skin can be chosen from a group that can include *Cyamopsis tetragonolobus* gum. Moreover, *Cyamopsis tetragonolobus* gum also has a binding and/or stabilizing and/or fragrance and/or viscous-making function for the structure of the formula.

A possible formula can consist of the following compounds: *Aloe barbadensis* leaf juice, *Centaurea cyanus* flower water, *Hamamelis virginiana* water, vegetable glycerin, coco-glucoside, arginine, malic acid, *Cyamopsis tetragonolobus* gum and ethyl lauroyl arginate HCl.

In particular, in the specific formula, *Aloe barbadensis* leaf juice goes from 75% to 100% w/w, *Centaurea cyanus* flower water goes from 1% to 5% w/w, *Hamamelis virginiana* water goes from 1% to 5% w/w, vegetable glycerin goes from 1% to 5% w/w, coco-glucoside goes from 0.1% to 1% w/w, arginine goes from 0.1% to 1% w/w, malic acid goes from 0.1% to 1% w/w, *Cyamopsis tetragonolobus* gum goes from 0.1% to 1% w/w and ethyl lauroyl arginate HCl goes from 0.1% to 1% w/w.

For example, the gel can be made in order to obtain a cosmetic composition to cleanse, detox, oxygenate and soothe the skin. Moreover, the cosmetic composition is able to keep the hydrolipidic layer of the skin unaltered.

In one embodiment, a cosmetic composition in gel form can include one or more compounds functional for the skin, such as a hydrating, washing active compound, a compound that maintains the skin in good condition.

Possible hydrating compounds for the skin can be chosen from a group that can comprise sorbitol, fructose, sterilized and demineralized water. Moreover, sorbitol can also have an aromatizing, fragrance, moisturizing function for the structure of the formula. Furthermore, fructose can also have a moisturizing and aromatizing function for the structure of the formula. The water can also have a solvent function for the structure of the formula.

Possible washing active compounds for the skin can be chosen from a group that can include cocamidopropyl betaine and sodium lauroyl sarcosinate.

Advantageously, one or more washing active compounds for the skin can also have a surfactant function for the skin. Moreover, cocamidopropyl betaine can also have a hydrating function for the skin and an anti/static and/or viscous-making function for the structure of the formula.

A possible compound that keeps the skin in good condition can be sea salt for example, which advantageously also has an abrasive function for the skin.

A possible formula can consist of the following compounds: sorbitol, fructose, sterilized and demineralized water, cocamidopropyl betaine, sodium lauroyl sarcosinate and sea salt.

In particular, in the specific formula, sorbitol goes from 25% to 50% w/w, fructose goes from 25% to 50% w/w, sterilized and demineralized water goes from 10% to 25% w/w, cocamidopropyl betaine goes from 5% to 10% w/w, sodium lauroyl sarcosinate goes from 1% to 5% w/w and sea salt goes from 0.1% to 1% w/w.

For example, the gel can be made in order to obtain a cosmetic composition able to keep the hydrolipidic layer unchanged and without altering the pH of the skin.

In a particular embodiment, the cosmetic composition can be a serum or fluid.

The serum or fluid can include one or more compounds with a solvent function for the structure of the formula and a hydrating function for the skin. For example, a solvent can be distilled or sterile water, or water mixed with alcohols, or hydrophilic compounds in general.

Hereafter we will refer to a cosmetic composition in which the solvent is water or hydrophilic compounds functional for the skin and not harmful for it. In particular, the serum or fluid can include distilled or sterile water as the only solvent for the structure of the skin.

In one embodiment, a cosmetic composition in serum or fluid form can include one or more compounds functional for the skin, such as a hydrating, anti-oxidant or firming compound.

A possible hydrating compound for the skin can be vegetable glycerin for example, which advantageously also has a protective function for the skin and a fragrance and/or moisturizing and/or viscosity-reducing function for the structure of the formula.

A possible anti-oxidant compound for the skin can be lactobionic acid for example, which advantageously also has a pH adjusting function of the skin.

A possible firming compound for the skin can be gluconolactone for example, which advantageously also has a fragrance function for the structure of the formula.

A possible formula can consist of the following compounds: vegetable glycerin, lactobionic acid and gluconolactone.

In particular, in the specific formula, vegetable glycerin goes from 75% to 100% w/w, lactobionic acid goes from 0.1% to 1% w/w and gluconolactone goes from 0.1% to 1% w/w.

For example, the serum or fluid can be made in order to obtain a cosmetic composition able to guarantee an anti-oxidant and anti-wrinkle effect, and able to increase the plumpness of the skin and help to prevent sunspots.

In one embodiment, a cosmetic composition in serum or fluid form can include one or more compounds functional for the skin, such as an anti-oxidant, hydrating, emollient.

Possible anti-oxidant compounds for the skin can be chosen from a group that can include *Hamamelis virginiana* water, ascorbic acid and glutathione.

Advantageously, one or more anti-oxidant compounds for the skin can also have an illuminator function for the skin, such as for example ascorbic acid and glutathione. Moreover, ascorbic acid can also have a hydrating and/or pH adjusting function for the skin, and a fragrance function for the structure of the formula. Furthermore, glutathione can also have a reducing agent and/or a fragrance function for the structure of the formula.

Advantageously, *Hamamelis virginiana* water can also have a soothing and/or hydrating and/or protective and/or astringent function for the skin.

A possible hydrating compound for the skin can be vegetable glycerin for example, which advantageously also has a protective function of the skin and a fragrance and/or moisturizing and/or viscosity-reducing function for the structure of the formula.

Possible emollient compounds for the skin can be chosen from a group that can include hydroxyethylcellulose and ethyl lauroyl arginate HCl.

Advantageously, hydroxyethylcellulose also has a binding and/or stabilizing and/or filmogenic and/or viscous-making function for the structure of the formula.

A possible formula can consist of the following compounds: *Hamamelis virginiana* water, ascorbic acid, vegetable glycerin, glutathione, hydroxyethylcellulose and ethyl lauroyl arginate HCl.

In particular, in the specific formula, *Hamamelis virginiana* water goes from 75% to 100% w/w, ascorbic acid goes from 5% to 10% w/w, vegetable glycerin goes from 1% to 5% w/w, glutathione is less than 0.1% w/w, hydroxyethylcellulose goes from 0.1% to 1% w/w and ethyl lauroyl arginate HCl goes from 0.1% to 1% w/w.

For example the serum or fluid can be made in order to obtain a cosmetic composition able to guarantee a revitalizing and anti-wrinkle effect, and able to stretch the skin and make it more radiant.

In one embodiment, a cosmetic composition in serum or fluid form can include one or more compounds functional for the skin, such as a nutrient, firming or soothing compound.

A possible nutrient compound for the skin can be vegetable glycerin for example, which advantageously also has a protective function of the skin and a fragrance and/or moisturizing and/or viscosity-reducing function for the structure of the formula.

A possible firming compound for the skin can be, for example, nano gum, which advantageously also has a viscous-making function for the structure of the formula.

A possible soothing compound for the skin can be panthenol for example, which advantageously also has the function of redeveloping the epithelium for the skin.

A possible formula can consist of the following compounds: vegetable glycerin, nano gum and panthenol.

In particular, in the specific formula vegetable glycerin goes from 50% to 75% w/w, natto gum goes from 25% to 50% w/w and panthenol goes from 5% to 10% w/w.

In one embodiment, a cosmetic composition in serum or fluid form can include one or more compounds functional for the skin, such as a hydrating, nutrient, soothing or anti-wrinkle compound.

A possible hydrating compound for the skin can be *Aloe barbadensis* leaf juice for example, which advantageously also has an anti-oxidant function for the skin.

A possible nutrient compound for the skin can be vegetable glycerin for example, which advantageously also has a protective function for the skin, and a fragrance and/or moisturizing and/or viscosity-reducing function for the structure of the formula.

A possible soothing compound for the skin can be panthenol for example, which advantageously also has a regenerating function for the skin.

A possible anti-wrinkle compound for the skin can be ubiquinone for example, which advantageously also has an anti-oxidant function for the skin and a miscellaneous function for the structure of the formula.

A possible formula can consist of the following compounds: *Aloe barbadensis* leaf juice, vegetable glycerin, panthenol and ubiquinone.

In particular, in the specific formula, *Aloe barbadensis* leaf juice goes from 75% to 100% w/w, vegetable glycerin goes from 10% to 25% w/w, panthenol goes from 5% to 10% w/w and ubiquinone goes from 0.1% to 1% w/w.

For example, the serum or fluid can be made in order to obtain a cosmetic composition able to prevent ageing of the skin on a cell level, to exert a soothing and compacting function and to rehydrate the skin.

In one embodiment, a cosmetic composition in serum or fluid form can include one or more compounds functional for the skin, such as a hydrating, anti-oxidant, pH adjuster and an emollient.

Possible hydrating compounds for the skin can be chosen from a group that can include: biosaccharide gum-1, sodium hyaluronate, hydrogenated lecithin, trehalose, sterilized and demineralized water.

Advantageously, biosaccharide gum-1 can also have a soothing function for the skin. Moreover, hydrogenated lecithin can also have a nutrient, anti-ageing function for the skin and a surfactant-emulsifying and/or suspendant function for the structure of the formula. The water can also have a solvent function for the structure of the formula. Furthermore, trehalose can also have a moisturizing function for the structure of the formula.

A possible anti-oxidant compound can be *Hamamelis virginiana* water for example, which advantageously also has a protective and/or hydrating and/or astringent function for the skin.

A possible pH adjuster compound for the skin can be lactic acid for example, which advantageously also has an exfoliant and/or hydrating function for the skin and a fragrance and/or moisturizing function for the structure of the formula.

Possible emollient compounds for the skin can be chosen from a group that can comprise glyceryl caprylate and glyceryl undecylenate.

Advantageously, glyceryl undecylenate can also have a surfactant-emulsifying function for the structure of the formula.

A possible formula can consist of the following compounds: *Hamamelis virginiana* water, biosaccharide gum-1, sodium hyaluronate, hydrogenated lecithin, trehalose, lactic acid, sterilized and demineralized water, glyceryl caprylate and glyceryl undecylenate.

In particular, in the specific formula, *Hamamelis virginiana* water goes from 75% to 100% w/w, biosaccharide gum-1 goes from 1% to 5% w/w, sodium hyaluronate goes from 0.1% to 1% w/w, hydrogenated lecithin goes from 0.1% to 1% w/w, trehalose is less than 0.1% w/w, lactic acid is less than 0.1% w/w, sterilized and demineralized water is less than 0.1% w/w, glyceryl caprylate goes from 0.1% to 1% w/w and glyceryl undecylenate goes from 0.1% to 1% w/w.

For example, the serum or fluid can be made in order to obtain a cosmetic composition able to prevent ageing of the skin, with a nutrient, soothing and anti-oxidant action for the skin. Moreover, the cosmetic composition contributes to give elasticity and plumpness to the skin.

In one embodiment, a cosmetic composition in serum or fluid form can include one or more compounds functional for the skin, such as a hydrating, soothing, anti-ageing, skin pH adjuster or emollient compound.

Possible hydrating compounds for the skin can be chosen from a group that can comprise sodium hyaluronate and sterilized and demineralized water. Moreover, the water can also have a solvent function for the structure of the formula.

A possible soothing compound can be *Hamamelis virginiana* water for example, which advantageously also has a protective and/or hydrating and/or astringent function for the skin.

Possible anti-ageing compounds for the skin can be chosen from a group that can comprise arginine and/or lysine polypeptide, which advantageously also have a tensing and/or hydrating effect for the skin.

A possible skin pH adjuster compound can be lactic acid for example, which advantageously also has an exfoliant and/or hydrating function for the skin and a fragrance and/or moisturizing function for the structure of the formula.

Possible emollient compounds for the skin can be chosen from a group that can include glyceryl caprylate and glyceryl undecylenate.

Advantageously, glyceryl undecylenate can also have a surfactant-emulsifying function for the structure of the formula.

A possible formula can consist of the following compounds: *Hamamelis virginiana* water, sodium hyaluronate, arginine and/or lysine polypeptide, sterilized and demineralized water, lactic acid, glyceryl caprylate and glyceryl undecylenate.

In particular, in the specific formula, *Hamamelis virginiana* water goes from 75% to 100% w/w, sodium hyaluronate goes from 0.1% to 1% w/w, arginine and/or lysine polypeptide is less than 0.1% w/w, sterilized and demineralized water goes from 0.1% to 1% w/w, lactic acid is less than 0.1% w/w, glyceryl caprylate goes from 0.1% to 1% w/w and glyceryl undecylenate goes from 0.1% to 1% w/w.

For example, the serum or fluid can be made in order to obtain a cosmetic composition able to treat specifically the untoned zones that are marked by aged skin.

In one embodiment, a cosmetic composition in serum or fluid form can include one or more compounds functional for the skin, such as a hydrating, exfoliant, emollient, moisturizing or pH adjuster compound.

Possible hydrating compounds for the skin can be chosen from a group that can include sterilized and demineralized water and vegetable glycerin. Moreover, the water can also have a solvent function for the structure of the formula. Furthermore, the vegetable glycerin can also have a protective function for the skin and a fragrance and/or moisturizing and/or viscosity-reducing function for the structure of the formula.

Advantageously, compounds with an exfoliant function can also have a renewal and/or pH adjuster function for the skin and a fragrance function for the structure of the formula.

Possible exfoliant compounds for the skin can be chosen from a group that can comprise malic acid, mandelic acid and tartaric acid.

A possible emollient can be ethyl lauroyl arginate HCl for example.

A possible moisturizing compound for the skin can be hydroxyethylcellulose for example, which advantageously also has a binding and/or stabilizing and/or filmogenic and/or viscous-making function for the structure of the formula.

A possible pH adjuster compound for the skin can be ammonium hydroxide for example, which advantageously also has a denaturing agent function for the structure of the formula.

A possible formula can consist of the following compounds: sterilized and demineralized water, vegetable glycerin, malic acid, mandelic acid, tartaric acid, ethyl lauroyl arginate HCl, hydroxyethylcellulose and ammonium hydroxide.

In particular, in the specific formula, sterilized and demineralized water goes from 75% to 100% w/w, vegetable glycerin goes from 10% to 25% w/w, malic acid goes from 0.1% to 1% w/w, mandelic acid goes from 0.1% to 1% w/w, tartaric acid goes from 0.1% to 1% w/w, ethyl lauroyl arginate HCl goes from 0.1% to 1% w/w, hydroxyethylcellulose goes from 0.1% to 1% w/w and ammonium hydroxide goes from 0.1% to 1% w/w.

In one embodiment, a cosmetic composition in serum or fluid form can include one or more compounds functional for the skin, such as a hydrating compound, a skin regenerator, an anti-oxidant, an illuminator, a hydrolipidic layer preserver, a skin renewal, an emollient.

Possible hydrating compounds for the skin can be chosen from a group that can comprise sterilized and demineralized water and sodium hyaluronate. Moreover, the water can also have a solvent function for the structure of the formula.

Advantageously, compounds with a skin regenerating function can also have an anti-oxidant and/or firming function for the skin.

Possible skin regenerating compounds for the skin can be chosen from a group that can comprise hydroxypropyl cyclodextrin and calcium ketogluconate. Moreover, hydroxypropyl cyclodextrin can also have a chelation agent function and stabilizing function for the structure of the formula.

A possible anti-oxidant compound can be *Helichrysum italicum* flower water for example, which advantageously can also have a soothing and/or hydrating function for the skin.

A possible illuminator compound for the skin can be 1-methylhydantoin-2-imide for example, which advantageously also has a hydrating function for the skin.

A possible compound that preserves the hydrolipidic film can be leuconostoc and/or radish root ferment filtrate for example, which advantageously also has an anti-microbe and/or anti-fungal function for the structure of the formula.

A possible skin renewal compound can be tripeptide-29 for example, which advantageously also has a hydrating function for the structure of the formula.

Possible emollient compounds for the skin can be chosen from a group that can comprise caprylyl glycol and 1,2-hexanediol. Moreover, 1,2-hexanediol can also have a solvent function for the structure of the formula.

A possible formula can consist of the following compounds: *Helichrysum italicum* flower water, hydroxypropyl cyclodextrin, sterilized and demineralized water, sodium hyaluronate, 1-methylhydantoin-2-imide, calcium ketogluconate, leuconostoc and/or radish root ferment filtrate, tripeptide-29, caprylyl glycol and 1,2-hexanediol.

In particular, in the specific formula, *Helichrysum italicum* flower water goes from 75% to 100% w/w, hydroxypropyl cyclodextrin goes from 5% to 10% w/w, sterilized and demineralized water goes from 5% to 10% w/w, sodium hyaluronate goes from 1% to 5% w/w, 1-methylhydantoin-2-imide goes from 0.1% to 1% w/w, calcium ketogluconate goes from 0.1% to 1% w/w, leuconostoc and/or radish root ferment filtrate is less than 0.1% w/w, tripeptide-29 goes from 0.1% to 1% w/w, caprylyl glycol goes from 0.1% to 1% w/w and 1,2-hexanediol goes from 0.1% to 1% w/w.

For example, the serum or fluid can be made in order to obtain a cosmetic composition with a skin regeneration effect.

In one embodiment, a cosmetic composition in serum or fluid form can include one or more compounds functional for the skin, such as a hydrating or a lifting compound.

A possible hydrating compound for the skin can be sterilized and demineralized water for example, which advantageously also has a solvent function for the structure of the formula.

A possible lifting compound for the skin can be sodium hyaluronate for example, which advantageously also has a hydrating function for the skin.

A possible formula can consist of the following compounds: sterilized and demineralized water and sodium hyaluronate.

In particular, in the specific formula, sterilized and demineralized water goes from 75% to 100% w/w, and sodium hyaluronate goes from 0.1% to 1% w/w.

For example, the serum or fluid can be made in order to obtain a cosmetic composition with an effect of elasticity, plumpness and hydration of the skin.

In a particular embodiment, the cosmetic composition can be an emulsion.

The emulsion can be multi-phase, for example two-phase, three-phase, four-phase, five-phase or even more.

Hereafter we will refer to an emulsion in which there is a lipophile phase, or oil phase, and an aqueous phase in which one or more water-soluble substances are dissolved in a solvent, for example water, or substances with a similar function. The cosmetic composition in emulsion form is made stable by using one or more compounds with an emulsifying function.

In one embodiment, a cosmetic composition in emulsion form can include one or more compounds functional for the skin, such as a hydrating, nutrient, anti-oxidant, emollient, anti-swelling, a pH adjuster or a regenerating compound and a compound to prevent dark circles under the eyes.

Possible hydrating compounds for the skin can be chosen from a group that can comprise sterilized and demineralized water and vegetable glycerin. Moreover, the water can also have a solvent function for the structure of the formula. Furthermore, the vegetable glycerin can also have a protective function for the skin and a fragrance and/or moisturizing and/or viscosity-reducing function for the structure of the formula.

Possible nutrient compounds for the skin can be chosen from a group that can comprise *Theobroma cacao* butter, cetearyl olivate, sorbitan olivate and *Argania spinosa* kernel oil.

Advantageously, *Argania spinosa* kernel oil can also have an anti-ageing and emollient function for the skin.

Moreover, *Theobroma cacao* butter can also have a protective function for the skin and a fragrance function for the structure of the formula.

Furthermore, sorbitan olivate can also have a surfactant and/or emulsifying function for the structure of the formula.

A possible anti-oxidant compound can be *Helichrysum italicum* flower water for example, which can also have a soothing and/or hydrating function for the skin.

Possible anti-oxidant compounds for the skin can be chosen from a group that can comprise *Hamamelis virginiana* water and tocopherol.

Advantageously, *Hamamelis virginiana* water can also have a soothing and/or protective and/or hydrating and/or astringent function for the skin.

Moreover, tocopherol can have a hydrating function for the skin and a fragrance function for the structure of the formula.

Possible emollient compounds for the skin can be chosen from a group that can comprise glyceryl caprylate, xanthan gum and glyceryl undecylenate.

Moreover, glyceryl caprylate can have a hydrating function for the skin.

Moreover, xanthan gum can have a hydrating function for the skin and a binding and/or stabilizing and/or surfactant and/or emulsifying and/or viscous-making function for the structure of the formula.

Moreover, glyceryl undecylenate can have a surfactant-emulsifying function for the structure of the formula.

Possible compounds to prevent dark circles under the eyes can be chosen from a group that can comprise hesperidin methyl chalcone, dipeptide-2, palmitoyl tetrapeptide-7.

Advantageously, one, or more or all the compounds to prevent dark circles under the eyes can also have a hydrating and/or anti-oxidant function for the skin and the function of preventing bags under the eyes.

A possible anti-swelling compound for the skin can be menthol for example, which advantageously also has a refreshing function for the skin and a denaturing agent and/or analgesic and/or aromatizing and/or fragrance function for the structure of the formula.

A possible pH adjuster compound can be sodium hydroxide for example, which advantageously also has a denaturing agent function for the skin.

A possible regenerating compound can be *Saccharomyces cerevisiae* extract for example, which advantageously also has a denaturing agent function for the skin.

A possible formula can consist of the following compounds: *Hamamelis virginiana* water, *Theobroma cacao* butter, cetearyl olivate, sterilized and demineralized water, sorbitan olivate, glyceryl caprylate, *Argania spinosa* kernel oil, vegetable glycerin, xanthan gum, glyceryl undecylenate, hesperidin methyl chalcone, menthol, tocopherol, dipeptide-2, sodium hydroxide, *Saccharomyces cerevisiae* extract and palmitoyl tetrapeptide-7.

In particular, in the specific formula, *Hamamelis virginiana* water goes from 75% to 100% w/w, *Theobroma cacao* butter goes from 1% to 5% w/w, cetearyl olivate goes from 1% to 5% w/w, sterilized and demineralized water goes from 1% to 5% w/w, sorbitan olivate goes from 1% to 5% w/w, glyceryl caprylate goes from 0.1% to 1% w/w, *Argania spinosa* kernel oil goes from 0.1% to 1% w/w, vegetable glycerin goes from 0.1% to 1% w/w, xanthan gum goes from 0.1% to 1% w/w, glyceryl undecylenate goes from 0.1% to 1% w/w, hesperidin methyl chalcone goes from 0.1% to 1% w/w, menthol goes from 0.1% to 1% w/w, tocopherol goes from 0.1% to 1% w/w, dipeptide-2 is less than 0.1% w/w, sodium hydroxide is less than 0.1% w/w, *Saccharomyces cerevisiae* extract is less than 0.1% w/w and palmitoyl tetrapeptide-7 is less than 0.1% w/w.

For example, the emulsion can be made in order to obtain a cosmetic composition that allows to drain excess liquids, to contrast loss of tone and elasticity of the skin and to contrast capillary fragility.

In one embodiment, a cosmetic composition in emulsion form can include one or more compounds functional for the skin, such as a nutrient, a balm, an anti-oxidant, an emollient, a refresher, a tan-prolonger.

Possible nutrient compounds for the skin can be chosen from a group that can comprise *Simmondsia chinensis* oil, cetearyl olivate, sorbitan olivate, *Persea gratissima* oil and oleic acid.

Advantageously, one or more or all the nutrient compounds can have an elasticiser and/or emollient and/or anti-ageing function for the skin.

Moreover, *Simmondsia chinensis* oil and *Persea gratissima* oil can also have a hydrating function for the skin.

Moreover, sorbitan olivate can also have a surfactant-emulsifying function for the structure of the formula.

Furthermore, oleic acid can also have a fragrance and/or surfactant-emulsifying function for the structure of the formula.

Possible soothing compounds for the skin can be chosen from a group that can comprise *Hamamelis virginiana* water, *Luffa cylindrica* seed oil and *Anthemis nobilis* oil.

Advantageously, *Hamamelis virginiana* water can also have an anti-oxidant and/or protective and/or hydrating and/or astringent function for the skin.

Moreover, *Luffa cylindrica* seed oil and *Anthemis nobilis* oil can have a hydrating function for the skin and/or a fragrance function for the structure of the formula.

A possible anti-oxidant compound can be smithsonite extract for example, which advantageously also has an anti-free radicals and/or hydrating function for the skin.

Possible emollient compounds for the skin can be chosen from a group that can comprise glyceryl caprylate, xanthan gum and glyceryl undecylenate.

Moreover, xanthan gum can also have a hydrating function for the skin and a binding and/or stabilizing and/or surfactant-emulsifying and/or viscous-making function for the structure of the formula.

Furthermore, glyceryl undecylenate can also have a surfactant-emulsifying function for the structure of the formula.

A possible refresher compound can be menthol for example, which advantageously also has a denaturing agent and/or analgesic and/or aromatizing and/or fragrance function for the structure of the formula.

A possible tan-prolonger compound can be oleoyl tyrosine for example, which advantageously also has a hydrating function for the skin.

A possible formula can consist of the following compounds: *Hamamelis virginiana* water, *Simmondsia chinensis* oil, cetearyl olivate, sorbitan olivate, *Persea gratissima* oil, oleoyl tyrosine, smithsonite extract, *Luffa cylindrica* seed oil, oleic acid, menthol, *Anthemis nobilis* oil, glyceryl caprylate, xanthan gum and glyceryl undecylenate In particular, in the specific formula, *Hamamelis virginiana* water goes from 75% to 100% w/w, *Simmondsia chinensis* oil goes from 5% to 10% w/w, cetearyl olivate goes from 1% to 5% w/w, sorbitan olivate goes from 1% to 5% w/w, *Persea gratissima* oil goes from 1% to 5% w/w, oleoyl tyrosine goes from 0.1% to 1% w/w, smithsonite extract goes from 0.1% to 1% w/w, *Luffa cylindrica* seed oil goes from 0.1% to 1% w/w, oleic acid goes from 0.1% to 1% w/w, menthol goes from 0.1% to 1% w/w, *Anthemis nobilis* oil is less than 0.1% w/w, glyceryl caprylate goes from 0.1% to 1% w/w, xanthan gum goes from 0.1% to 1% w/w and glyceryl undecylenate goes from 0.1% to 1% w/w.

For example, the emulsion can be made in order to obtain a cosmetic composition that allows to perform a soothing action and to preserve the tan. The emulsion also contrasts ageing and reduces the damage caused by free radicals.

In one embodiment, a cosmetic composition in emulsion form can include one or more compounds functional for the skin, such as a nutrient, a balm, an anti-oxidant, an emollient, an anti-ageing, a tan-activator, an illuminator, a tan-stimulant.

Possible nutrient compounds for the skin can be chosen from a group that can comprise *Moringa oleifera* seed oil, cetearyl olivate, sorbitan olivate, *Prunus armeniaca* kernel oil, *Elaeis guineensis* oil, squalene, phytosterols and *Glycine soja* oil.

Advantageously, *Moringa oleifera* seed oil, *Elaeis guineensis* oil and phytosterols can also have an elasticizing and/or hydrating function for the skin.

Advantageously, *Prunus armeniaca* kernel oil can also have an anti-oxidant and/or hydrating function for the skin and a fragrance function for the structure of the formula.

Moreover, sorbitan olivate can also have a surfactant-emulsifying function for the structure of the formula.

Moreover, squalene can have an emollient function for the skin.

Furthermore, *Glycine soja* oil can have an anti-oxidant and/or hydrating function for the skin and a fragrance function for the structure of the formula.

Possible soothing compounds for the skin can be chosen from a group that can comprise *Hamamelis virginiana* water and *Anthemis nobilis* oil.

Advantageously, *Hamamelis virginiana* water can have an anti-oxidant and/or protective and/or hydrating and/or astringent function for the skin.

Moreover, *Anthemis nobilis* oil can have a hydrating function for the skin and a fragrance function for the structure of the formula.

Possible anti-oxidant compounds for the skin can be chosen from a group that can comprise tocotrienols, tocopherol and *Rosmarinus officinalis* extract.

Advantageously, one or more or all the anti-oxidant compounds can also have an anti-ageing and/or hydrating and/or UV ray absorbing function for the skin. Moreover, tocopherol can also have a fragrance function for the structure of the formula.

Possible emollient compounds for the skin can be chosen from a group that can comprise xanthan gum, glyceryl caprylate and glyceryl undecylenate.

Advantageously, xanthan gum can also have a hydrating function for the skin and a binding and/or stabilizing and/or surfactant-emulsifying and/or viscous-making function for the structure of the formula.

Moreover, glyceryl undecylenate can also have a surfactant-emulsifying function for the structure of the formula.

A possible anti-ageing compound can be ubiquinone for example, which advantageously can also have a hydrating and/or anti-oxidant function for the skin.

A possible suntan activating compound can be *Mauritia flexuosa* oil for example, which advantageously can also have a hydrating function for the skin.

A possible illuminator compound can be *Phyllanthus emblica* extract for example, which advantageously can also have an anti-oxidant function for the skin.

A possible tan-stimulating compound can be beta carotene for example, which advantageously can also have a colorant function for the structure of the formula.

A possible formula can consist of the following compounds: *Hamamelis virginiana* water, *Moringa oleifera* seed oil, cetearyl olivate, sorbitan olivate, *Prunus armeniaca* kernel oil, *Mauritia flexuosa* oil, tocotrienols, *Elaeis guineensis* oil, tocopherol, squalene, phytosterols, ubiquinone, *Phyllanthus emblica* extract, xanthan gum, *Anthemis nobilis* oil, *Glycine soja* oil, *Rosmarinus officinalis* extract, glyceryl caprylate, glyceryl undecylenate and beta carotene.

In particular, in the specific formula, *Hamamelis virginiana* water goes from 75% to 100% w/w, *Moringa oleifera* seed oil goes from 5% to 10% w/w, cetearyl olivate goes from 1% to 5% w/w, sorbitan olivate goes from 1% to 5% w/w, *Prunus armeniaca* kernel oil goes from 1% to 5% w/w, *Mauritia flexuosa* oil goes from 0.1% to 1% w/w, tocotrienols is less than 0.1% w/w, *Elaeis guineensis* oil is less than 0.1% w/w, tocopherol is less than 0.1% w/w, squalene is less than 0.1% w/w, phytosterols is less than 0.1% w/w, ubiquinone is less than 0.1% w/w, *Phyllanthus emblica* extract goes from 0.1% to 1% w/w, xanthan gum goes from 0.1% to 1% w/w, *Anthemis nobilis* oil is less than 0.1% w/w, *Glycine soja* oil is less than 0.1% w/w, *Rosmarinus officinalis* extract is less than 0.1% w/w, glyceryl caprylate goes from 0.1% to 1% w/w, glyceryl undecylenate goes from 0.1% to 1% w/w and beta carotene is less than 0.1% w/w.

For example, the emulsion can be made in order to obtain a cosmetic composition that allows to obtain an intense and luminous tan and at the same time to reinforce the natural defenses of the skin to contrast the harmful effects deriving from exposure to UV rays. The emulsion also prevents ageing and reduces the oxidizing damage caused by exposure to the sun.

In one embodiment, a cosmetic composition in emulsion form can include one or more compounds functional for the skin, such as a nutrient, a balm, a hydrating, an anti-oxidant, an emollient, an energizer, a fragrance.

Possible nutrient compounds for the skin can be chosen from a group that can comprise cetearyl olivate, *Macadamia ternifolia* seed oil, sorbitan olivate, glyceryl stearate, *Astrocaryum murumuru* seed butter, *Astrocaryum tucuma* seed butter, *Prunus armeniaca* kernel oil, *Helianthus annuus* seed oil and cetyl palmitate.

Advantageously, one or more or all the nutrient compounds can also have a soothing and/or hydrating and/or emollient function for the skin.

Moreover, sorbitan olivate and glyceryl stearate can also have a surfactant-emulsifying function for the structure of the formula.

Furthermore, glyceryl stearate, *Prunus armeniaca* kernel oil and cetyl palmitate can also have a fragrance function for the structure of the formula.

A possible soothing compound can be *Aloe barbadensis* leaf juice for example, which advantageously can also have a hydrating function for the skin.

A possible hydrating compound can be trehalose for example, which advantageously can also have an aromatizing and/or moisturizing function for the structure of the formula.

Possible anti-oxidant compounds for the skin can be chosen from a group that can comprise tocopherol, *Citrus aurantium bergamia* peel oil, *Citrus aurantium dulcis* peel oil and *Citrus limon* peel oil.

Advantageously, one or more or all the anti-oxidant compounds can also have a hydrating function for the skin and/or a fragrance function for the structure of the formula.

Possible emollient compounds for the skin can be chosen from a group that can comprise xanthan gum, sorbitan palmitate, glyceryl caprylate and glyceryl undecylenate.

Moreover, xanthan gum can also have a hydrating function for the skin and a binding and/or stabilizing and/or surfactant-emulsifying and/or viscous-making function for the structure of the formula.

Moreover, sorbitan palmitate and glyceryl undecylenate can also have a surfactant-emulsifying function for the structure of the formula.

Possible energizing compounds for the skin can be chosen from a group that can comprise *Abies sibirica* oil, *Artemisia herba-alba* herb oil, *Barosma betulina* leaf oil, *Cinnamomum camphora* bark oil, *Cinnamomum camphora* leaf oil, *Copaifera officinalis* resin, *Cymbopogon martini* oil, *Ferula galbaniflua* resin oil, *Tagetes minuta* oil, *Salvia sclarea* oil and *Mentha spicata* herb oil.

Advantageously, one or more or all the energizing compounds can also have a hydrating function for the skin and a fragrance and/or filmogenic function for the structure of the cosmetic composition.

Possible compounds having a fragrance function for the skin can be chosen from a group that can comprise limonene, linalool, geraniol and citral.

Moreover, limonene can also have a solvent function for the structure of the formula.

Furthermore, citral can also have an aromatizing function for the structure of the formula.

A possible formula can consist of the following compounds: *Aloe barbadensis* leaf juice, cetearyl olivate, *Macadamia ternifolia* seed oil, sorbitan olivate, glyceryl stearate, *Astrocaryum murumuru* seed butter, *Astrocaryum tucuma* seed butter, trehalose, *Prunus armeniaca* kernel oil, *Helianthus annuus* seed oil, cetyl palmitate, tocopherol, xanthan gum, *Abies sibirica* oil, *Artemisia herba-alba* herb oil, *Barosma betulina* leaf oil, *Cinnamomum camphora* bark oil, *Cinnamomum camphora* leaf oil, *Citrus aurantium bergamia* peel oil, *Citrus aurantium dulcis* peel oil, *Citrus limon* peel oil, *Copaifera officinalis* resin, *Cymbopogon martini* oil, *Ferula galbaniflua* resin oil, *Tagetes minuta* oil, *Salvia sclarea* oil, *Mentha spicata* herb oil, limonene, linalool, geraniol, citral, sorbitan palmitate, glyceryl caprylate and glyceryl undecylenate.

In particular, in the specific formula, *Aloe barbadensis* leaf juice goes from 75% to 100% w/w, cetearyl olivate goes from 1% to 5% w/w, *Macadamia ternifolia* seed oil goes from 1% to 5% w/w, sorbitan olivate goes from 1% to 5% w/w, glyceryl stearate goes from 1% to 5% w/w, *Astrocaryum murumuru* seed butter goes from 1% to 5% w/w, *Astrocaryum tucuma* seed butter goes from 1% to 5% w/w, trehalose goes from 1% to 5% w/w, *Prunus armeniaca* kernel oil goes from 0.1% to 1% w/w, *Helianthus annuus* seed oil goes from 0.1% to 1% w/w, cetyl palmitate goes from 0.1% to 1% w/w, tocopherol goes from 0.1% to 1% w/w, xanthan gum goes from 0.1% to 1% w/w, *Abies sibirica* oil is less than 0.1% w/w, *Artemisia herba-alba* herb oil is less than 0.1% w/w, *Barosma betulina* leaf oil is less than 0.1% w/w, *Cinnamomum camphora* bark oil is less than 0.1% w/w, *Cinnamomum camphora* leaf oil is less than 0.1% w/w, *Citrus aurantium bergamia* peel oil is less than 0.1% w/w, *Citrus aurantium dulcis* peel oil is less than 0.1% w/w, *Citrus limon* peel oil is less than 0.1% w/w, *Copaifera officinalis* resin is less than 0.1% w/w, *Cymbopogon martini* oil is less than 0.1% w/w, *Ferula galbaniflua* resin oil is less than 0.1% w/w, *Tagetes minuta* oil is less than 0.1% w/w, *Salvia sclarea* oil is less than 0.1% w/w, *Mentha spicata* herb oil is less than 0.1% w/w, limonene is less than 0.1% w/w, linalool is less than 0.1% w/w, geraniol is less than 0.1% w/w, citral is less than 0.1% w/w, sorbitan palmitate goes from 0.1% to 1% w/w, glyceryl caprylate goes from 0.1% to 1% w/w and glyceryl undecylenate goes from 0.1% to 1% w/w.

For example, the emulsion can be made in order to obtain a cosmetic composition with a soothing, nutrient and emollient action, with a mix of energizing substances.

In one embodiment, a cosmetic composition in emulsion form can include one or more compounds functional for the skin such as a nutrient, hydrating, anti-oxidant, emollient, restructuring, toning, illuminator, pH adjuster and anti-ageing compound.

Possible nutrient compounds for the skin can be chosen from a group that can comprise *Butyrospermum parkii* butter, *Prunus amygdalus dulcis* oil, triglycerides C10-18 and *Cocos nucifera* oil.

Advantageously, one or more or all the nutrient compounds can also have an anti-ageing and/or hydrating and/or elasticizing function for the skin and a viscous-making and/or fragrance and/or solvent function for the structure of the formula.

A possible hydrating compound can be sterilized and demineralized water for example, which advantageously can also have a solvent function for the structure of the formula.

Possible anti-oxidant compounds for the skin can be chosen from a group that can comprise limonene, *Rubus idaeus* seed oil, *Citrus limon* peel oil, *Citrus aurantium dulcis* peel oil, *Citrus aurantium bergamia* peel oil, *Cymbopogon citratus* leaf oil, citral and linalool.

Advantageously, one or more or all the anti-oxidant compounds can also have an energizing function for the skin and a fragrance function for the structure of the formula.

Moreover, limonene can also have a solvent function for the structure of the formula.

Moreover, *Citrus aurantium dulcis* peel oil and *Citrus aurantium bergamia* peel oil can also have a hydrating function for the skin.

Citral can also have an aromatizing function for the structure of the formula.

Furthermore, *Rubus idaeus* seed oil can also have an emollient function for the skin.

Possible emollient compounds for the skin can be chosen from a group that can comprise ethylhexyl cocoate, polyglyceryl-3 dicitrate and/or stearate, propanediol, glyceryl stearate, glyceryl stearate SE, myristyl myristate, glyceryl caprylate, caprylyl glycol, 1,2-hexanediol, *Cyamopsis tetragonolobus* gum, glyceryl undecylenate and *Copaifera officinalis* resin.

Advantageously, one or more or all the emollient compounds can also have a surfactant-emulsifying function for the structure of the formula.

Moreover, propanediol and 1,2-hexanediol can also have a solvent function and/or as an agent to reduce viscosity for the structure of the formula.

Moreover, myristyl myristate and glyceryl caprylate can also have a hydrating function for the skin.

Furthermore, *Cyamopsis tetragonolobus* gum can also have a binding and/or stabilizing and/or viscous-making function for the structure of the formula. *Copaifera officinalis* resin can also have a filmogenic function for the structure of the formula.

A possible restructuring compound can be *Echium plantagineum* seed oil for example, which advantageously can also have an elasticizing and/or hydrating function for the skin and a solvent function for the structure of the formula.

A possible toning compound can be *Rosa centifolia* flower water for example, which advantageously can also have a de-congestion and/or hydrating function for the skin.

A possible illuminator compound can be phytic acid for example, which advantageously can also have a chelation agent function for the structure of the formula.

A possible pH adjuster compound can be sodium hydroxide for example, which advantageously can also have a denaturing function for the structure of the formula. A possible anti-ageing compound can be superoxide dismutase for example, which advantageously can also have a hydrating function for the skin and a reducing agent function for the structure of the formula.

One embodiment can consist of the following compounds: *Rosa centifolia* flower water, ethylhexyl cocoate, *Butyrospermum parkii* butter, polyglyceryl-3 dicitrate and/or stearate, *Prunus amygdalus dulcis* oil, propanediol, triglycerides C10-18, glyceryl stearate, glyceryl stearate SE, *Echium plantagineum* seed oil, myristyl myristate, *Cocos nucifera* oil, glyceryl caprylate, caprylyl glycol, 1,2-hexanediol, *Cyamopsis tetragonolobus* gum, sterilized and demineralized water, glyceryl undecylenate, limonene, *Rubus idaeus* seed oil, phytic acid, *Citrus limon* peel oil, *Citrus aurantium dulcis* peel oil, *Citrus aurantium bergamia* peel oil, *Cymbopogon citratus* leaf oil, *Copaifera officinalis* resin, citral, linalool, sodium hydroxide and superoxide dismutase.

In particular, in the specific formula, *Rosa centifolia* flower water goes from 50% to 75% w/w, ethylhexyl cocoate goes from 1% to 5% w/w, *Butyrospermum parkii* butter goes from 1% to 5% w/w, polyglyceryl-3 dicitrate and/or stearate goes from 1% to 5% w/w, *Prunus amygdalus dulcis* oil goes from 1% to 5% w/w, propanediol goes from 1% to 5% w/w, triglycerides C10-18 goes from 1% to 5% w/w, glyceryl stearate goes from 1% to 5% w/w, glyceryl stearate SE goes from 1% to 5% w/w, *Echium plantagineum* seed oil goes from 0.1% to 1% w/w, myristyl myristate goes from 0.1% to 1% w/w, *Cocos nucifera* oil goes from 0.1% to 1% w/w, glyceryl caprylate goes from 0.1% to 1% w/w, caprylyl glycol goes from 0.1% to 1% w/w, 1,2-hexanediol goes from 0.1% to 1% w/w, *Cyamopsis tetragonolobus* gum goes from 0.1% to 1% w/w, sterilized and demineralized water goes from 0.1% to 1% w/w, glyceryl undecylenate goes from 0.1% to 1% w/w, limonene is less than 0.1% w/w, *Rubus idaeus* seed oil is less than 0.1% w/w, phytic acid is less than 0.1% w/w, *Citrus limon* peel oil is less than 0.1% w/w, *Citrus aurantium dulcis* peel oil is less than 0.1% w/w, *Citrus aurantium bergamia* peel oil is less than 0.1% w/w, *Cymbopogon citratus* leaf oil is less than 0.1% w/w, *Copaifera officinalis* resin is less than 0.1% w/w, citral is less than 0.1% w/w, linalool is less than 0.1% w/w, sodium hydroxide is less than 0.1% w/w and superoxide dismutase is less than 0.1% w/w.

For example, the emulsion can be made in order to obtain a cosmetic composition with a nutrient and hydrating action. Moreover, the emulsion has anti-oxidant properties to contrast free radicals, which cause ageing of the skin.

In one embodiment, a cosmetic composition in emulsion form can include one or more compounds functional for the skin, such as a nutrient, a hydrating, an anti-oxidant, an emollient, an energizer, a toner or an anti-ageing compound.

Possible nutrient compounds for the skin can be chosen from a group that can comprise ethylhexyl cocoate, *Butyrospermum parkii* butter, polyglyceryl-3 dicitrate and/or stearate, *Prunus amygdalus dulcis* oil, myristyl myristate, *Acacia decurrens* and/or jojoba and/or sunflower seed wax polyglyceryl-3 esters, triglycerides C10-18, glyceryl stearate, jojoba oil and/or macadamia seed oil esters, squalene, *Theobroma cacao* seed butter, *Prunus persica* kernel oil, hydrogenated vegetable oil, *Cocos nucifera* oil, *Pelargonium graveolens* flower oil, *Pogostemon cablin* oil, *Tagetes minuta* oil and *Salvia sclarea* oil.

Advantageously, one or more or all the nutrient compounds can also have an elasticizer and/or anti-ageing and/or hydrating and/or emollient and/or protective function for the skin and a viscous-making and/or surfactant-emulsifying and/or fragrance and/or solvent function for the structure of the formula.

Possible hydrating compounds for the skin can be chosen from a group that can include vegetable glycerin, sodium hyaluronate and sterilized and demineralized water.

Moreover, vegetable glycerin can also have a protective function for the skin and a moisturizing and/or viscosity-reducing and/or fragrance function for the structure of the formula.

Moreover, sodium hyaluronate can also have an absorbent and/or binding and/or stabilizing and/or suspension agent function for the structure of the formula.

Furthermore, water can have a solvent function for the structure of the formula.

A possible anti-oxidant compound can be *Vigna aconitifolia* seed extract for example, which advantageously can also have a hydrating function for the skin.

Possible emollient compounds for the skin can be chosen from a group that can comprise, xanthan gum, lactic acid, caprylyl glycol, 1,2-hexanediol, glyceryl caprylate and glyceryl undecylenate.

Moreover, xanthan gum and glyceryl undecylenate can also have a hydrating function for the skin and a binding and/or stabilizing and/or surfactant-emulsifying and/or viscous-making function for the structure of the formula.

Moreover, lactic acid can also have an exfoliant, pH adjuster, hydrating function for the skin and a moisturizing and fragrance function for the structure of the formula.

Furthermore, 1,2-hexanediol can also have a solvent function for the structure of the formula.

Possible energizing compounds for the skin can be chosen from a group that can comprise *Copaifera officinalis* resin, *Cymbopogon winterianus* herb oil, *Amyris balsamifera* bark oil, *Cedrus atlantica* wood oil, *Citrus aurantium amara* leaf/twig oil, *Citrus aurantium bergamia* peel oil and *Citrus aurantium dulcis* peel oil.

Advantageously, one or more or all the energizing compounds can also have a hydrating function for the skin and a fragrance and/or filmogenic function for the structure of the formula.

A possible toning compound can be *Rosa centifolia* flower water for example, which advantageously can also have a decongestant and/or hydrating function for the skin.

Possible anti-ageing compounds for the skin can be chosen from a group that can comprise phytosteryl macadamiate, phytosterols, tocopherol, mannitol, acetyl tetrapeptide-11 and maltodextrin.

Advantageously, one or more or all the anti-ageing compounds can also have a hydrating, anti-oxidant function for the skin and a fragrance and/or binding and/or aromatizing and/or moisturizing and/or stabilizing function for the structure of the formula.

A possible formula can consist of the following compounds: *Rosa centifolia* flower water, vegetable glycerin, ethylhexyl cocoate, *Butyrospermum parkii* butter, polyglyceryl-3 dicitrate and/or stearate, *Prunus amygdalus dulcis* oil, myristyl myristate, *Acacia decurrens* and/or jojoba and/or sunflower seed wax polyglyceryl-3 esters, triglycerides C10-18, glyceryl stearate, jojoba oil and/or macadamia seed oil esters, squalene, phytosteryl macadamiate, phytosterols, tocopherol, *Theobroma cacao* seed butter, *Prunus persica* kernel oil, hydrogenated vegetable oil, mannitol, acetyl tetrapeptide-11, *Vigna aconitifolia* seed extract, maltodextrin, sodium hyaluronate, *Cocos nucifera* oil, *Pelargonium graveolens* flower oil, *Pogostemon cablin* oil, *Tagetes minuta* oil, *Salvia sclarea* oil, *Copaifera officinalis* resin, *Cymbopogon winterianus* herb oil, *Amyris balsamifera* bark oil, *Cedrus atlantica* wood oil, *Citrus aurantium amara* leaf/twig oil, *Citrus aurantium bergamia* peel oil, *Citrus aurantium dulcis* peel oil, xanthan gum, sterilized and demineralized water, lactic acid, caprylyl glycol, 1,2-hexanediol, glyceryl caprylate and glyceryl undecylenate.

In particular, in the specific formula, *Rosa centifolia* flower water goes from 50% to 75% w/w, vegetable glycerin goes from 5% to 10% w/w, ethylhexyl cocoate goes from 1% to 5% w/w, *Butyrospermum parkii* butter goes from 1% to 5% w/w, polyglyceryl-3 dicitrate and/or stearate goes from 1% to 5% w/w, *Prunus amygdalus dulcis* oil goes from 1% to 5% w/w, myristyl myristate goes from 1% to 5% w/w, *Acacia decurrens* and/or jojoba and/or sunflower seed wax polyglyceryl-3 esters goes from 1% to 5% w/w, triglycerides C10-18 goes from 1% to 5% w/w, glyceryl stearate goes from 1% to 5% w/w, jojoba oil and/or macadamia seed oil esters goes from 0.1% to 1% w/w, squalene goes from 0.1% to 1% w/w, phytosteryl macadamiate is less than 0.1% w/w, phytosterols is less than 0.1% w/w, tocopherol is less than 0.1% w/w, *Theobroma cacao* seed butter goes from 0.1% to 1% w/w, *Prunus persica* kernel oil goes from 0.1% to 1% w/w, hydrogenated vegetable oil goes from 0.1% to 1% w/w, mannitol goes from 0.1% to 1% w/w, acetyl tetrapeptide-11 is less than 0.1% w/w, *Vigna aconitifolia* seed extract goes from 0.1% to 1% w/w, maltodextrin is less than 0.1% w/w, sodium hyaluronate is less than 0.1% w/w, *Cocos nucifera* oil goes from 0.1% to 1% w/w, *Pelargonium graveolens* flower oil is less than 0.1% w/w, *Pogostemon cablin* oil is less than 0.1% w/w, *Tagetes minuta* oil is less than 0.1% w/w, *Salvia sclarea* oil is less than 0.1% w/w, *Copaifera*

*officinalis* resin is less than 0.1% w/w, *Cymbopogon winterianus* herb oil is less than 0.1% w/w, *Amyris balsamifera* bark oil is less than 0.1% w/w, *Cedrus atlantica* wood oil is less than 0.1% w/w, *Citrus aurantium amara* leaf/twig oil is less than 0.1% w/w, *Citrus aurantium bergamia* peel oil is less than 0.1% w/w, *Citrus aurantium dulcis* peel oil is less than 0.1% w/w, xanthan gum goes from 0.1% to 1% w/w, sterilized and demineralized water is less than 0.1% w/w, lactic acid is less than 0.1% w/w, caprylyl glycol is less than 0.1% w/w, 1,2-hexanediol is less than 0.1% w/w, glyceryl caprylate is less than 0.1% w/w and glyceryl undecylenate is less than 0.1% w/w.

For example, the emulsion can be made in order to obtain a cosmetic composition with an anti-ageing and nutrient action.

In one embodiment, a cosmetic composition in emulsion form can include one or more compounds functional for the skin, such as a nutrient, hydrating, soothing, anti-oxidant, emollient, oxidant, pH adjuster and anti-ageing compound.

Possible nutrient compounds for the skin can be chosen from a group that can comprise *Simmondsia chinensis* seed oil, *Butyrospermum parkii* butter, *Persea gratissima* oil unsaponifiables, triglycerides C10-18, *Acacia decurrens* and/or jojoba and/or sunflower seed wax polyglyceryl-3 esters.

Advantageously, one or more or all the nutrient compounds can also have an anti-ageing and/or hydrating function for the skin and a viscous-making and/or solvent function for the structure of the formula.

Possible hydrating compounds for the skin can be chosen from a group that can comprise sterilized and demineralized water and vegetable glycerin.

Moreover, vegetable glycerin can also have a protective function for the skin and a moisturizing and/or viscosity-reducing and/or fragrance function for the structure of the formula.

Moreover, the water can also have a solvent function for the structure of the formula.

A possible soothing compound can be *Anthemis nobilis* flower oil for example, which advantageously can also have a hydrating function for the skin and a fragrance function for the structure of the formula.

Possible anti-oxidant compounds for the skin can be chosen from a group that can comprise *Hamamelis virginiana* water and tocopherol.

Moreover, *Hamamelis virginiana* water can also have a hydrating, protective and astringent function for the skin.

Moreover, tocopherol can also have a hydrating function for the skin and a fragrance function for the structure of the formula.

Possible emollient compounds for the skin can be chosen from a group that can comprise glyceryl stearate, glyceryl stearate SE, propanediol, myristyl myristate, glyceryl caprylate, glyceryl dibehenate, 1,2-hexanediol, caprylyl glycol, xanthan gum, glyceryl undecylenate and disodium succinate.

Advantageously, one or more or all the emollient compounds can also have a hydrating function for the skin and a fragrance and/or surfactant-emulsifying and/or solvent and/or viscosity-reducing agent and/or binding and/or stabilizing function for the structure of the formula.

Moreover, xanthan gum can also have a viscous-making function for the structure of the formula.

A possible oxidant compound can be *Saccharomyces* lysate for example, which advantageously can also have a hydrating function for the skin.

A possible pH adjuster compound can be sodium hydroxide for example, which advantageously can also have a denaturing agent function for the structure of the formula.

Possible anti-ageing compounds for the skin can be chosen from a group that can comprise phytic acid, glutamic acid, glycine, threonine and valine.

Advantageously, one or more or all the anti-ageing compounds can also have a hydrating function for the skin and a fragrance and/or moisturizing and/or buffer agent and/or chelation agent function for the structure of the formula.

One embodiment can consist of the following compounds: *Hamamelis virginiana* water, *Simmondsia chinensis* seed oil, *Butyrospermum parkii* butter, glyceryl stearate, glyceryl stearate SE, *Persea gratissima* oil unsaponifiables, propanediol, triglycerides C10-18, *Acacia decurrens* and/or jojoba and/or sunflower seed wax polyglyceryl-3 esters, myristyl myristate, glyceryl caprylate, glyceryl dibehenate, 1,2-hexanediol, caprylyl glycol, tocopherol, sterilized and demineralized water, xanthan gum, glyceryl undecylenate, vegetable glycerin, sodium hydroxide, phytic acid, *Anthemis nobilis* flower oil, *Saccharomyces* lysate, disodium succinate, glutamic acid, glycine, threonine and valine.

In particular, in the specific formula, *Hamamelis virginiana* water goes from 50% to 75% w/w, *Simmondsia chinensis* seed oil goes from 5% to 10% w/w, *Butyrospermum parkii* butter goes from 5% to 10% w/w, glyceryl stearate goes from 5% to 10% w/w, glyceryl stearate SE goes from 5% to 10% w/w, *Persea gratissima* oil unsaponifiables goes from 5% to 10% w/w, propanediol goes from 5% to 10% w/w, triglycerides C10-18 goes from 5% to 10% w/w, *Acacia decurrens* and/or jojoba and/or sunflower seed wax polyglyceryl-3 esters goes from 0.1% to 1% w/w, myristyl myristate goes from 0.1% to 1% w/w, glyceryl caprylate goes from 0.1% to 1% w/w, glyceryl dibehenate goes from 0.1% to 1% w/w, 1,2-hexanediol goes from 0.1% to 1% w/w, caprylyl glycol goes from 0.1% to 1% w/w, tocopherol goes from 0.1% to 1% w/w, sterilized and demineralized water goes from 0.1% to 1% w/w, xanthan gum goes from 0.1% to 1% w/w, glyceryl undecylenate goes from 0.1% to 1% w/w, vegetable glycerin is less than 0.1% w/w, sodium hydroxide is less than 0.1% w/w, phytic acid is less than 0.1% w/w, *Anthemis nobilis* flower oil is less than 0.1% w/w, *Saccharomyces* lysate is less than 0.1% w/w, disodium succinate is less than 0.1% w/w, glutamic acid is less than 0.1% w/w, glycine is less than 0.1% w/w, threonine is less than 0.1% w/w and valine is less than 0.1% w/w.

For example, the emulsion can be made in order to obtain a cosmetic composition with a nutrient anti-ageing action and to stimulate cell breathing, that is, the regeneration of the skin.

It is clear that modifications and/or additions of parts may be made to the cosmetic composition as described heretofore, without departing from the field and scope of the present invention.

It is also clear that, although the present invention has been described with reference to some specific examples, a person of skill in the art shall certainly be able to achieve many other equivalent forms of cosmetic composition, having the characteristics as set forth in the claims and hence all coming within the field of protection defined thereby.

Although the above refers to embodiments of the invention, other embodiments can be provided without departing from the main field of protection, which is defined by the following claims.

The invention claimed is:

1. A cosmetic composition for healing and treating the skin, the formula of which consists exclusively of compounds functional for the skin and/or compounds functional both for the skin and also for the structure of the formula, and which does not comprise compounds exclusively functional for the structure of the formula, wherein the compounds functional for the skin have at least one function selected from a group consisting of hydrating, nutrient, anti-oxidant, emollient, anti-swelling, pH adjusting, regenerating, preventing dark circles under eyes, balm, refreshing, tan-prolonger, elasticizing, anti-aging, soothing, anti-free radicals, tan-activator, illuminator, tan-stimulant, energizer, restructuring and toning, said cosmetic composition is an emulsion, the cosmetic composition does not comprise silicons, petroleum jellies, and preservatives, and said emulsion consists of

*Hamamelis virginiana* water, *Simmondsia chinensis* oil, cetearyl olivate, sorbitan olivate, *Persea gratissima* oil, oleoyl tyrosine, smithsonite extract, *Luffa cylindrica* seed oil, oleic acid, menthol, *Anthemis nobilis* oil, glyceryl caprylate, xanthan gum, and glyceryl undecylenate.

2. The cosmetic composition as in claim 1, wherein said *Hamamelis virginiana* water is 75% w/w or more, said *Simmondsia chinensis* oil ranges from 5% to 10% w/w, said cetearyl olivate ranges from 1% to 5% w/w, said sorbitan olivate ranges from 1% to 5% w/w, said *Persea gratissima* oil ranges from 1% to 5% w/w, said oleoyl tyrosine ranges from 0.1% to 1% w/w, said smithsonite extract ranges from 0.1% to 1% w/w, said *Luffa cylindrica* seed oil ranges from 0.1% to 1% w/w, said oleic acid ranges from 0.1% to 1% w/w, said menthol ranges from 0.1% to 1% w/w, said *Anthemis nobilis* oil is less than 0.1% w/w, said glyceryl caprylate ranges from 0.1% to 1% w/w, said xanthan gum ranges from 0.1% to 1% w/w and said glyceryl undecylenate ranges from 0.1% to 1% w/w.

3. A cosmetic composition consisting of:
   75% w/w or more of *Hamamelis virginiana* water;
   5% to 10% w/w of *Simmondsia chinensis* oil;
   1% to 5% w/w of cetearyl olivate;
   1% to 5% w/w of sorbitan olivate;
   1% to 5% w/w of *Persea gratissima* oil;
   0.1% to 1% w/w of oleoyl tyrosine;
   0.1% to 1% w/w of smithsonite extract;
   0.1% to 1% w/w of *Luffa cylindrica* seed oil;
   0.1% to 1% w/w of oleic acid;
   0.1% to 1% w/w of menthol;
   less than 0.1% w/w of *Anthemis nobilis* oil;
   0.1% to 1% w/w of glyceryl caprylate;
   0.1% to 1% w/w of xanthan gum; and
   0.1% to 1% w/w of glyceryl undecylenate.

4. The cosmetic composition as in claim 3, wherein said cosmetic composition is an emulsion.

* * * * *